(12) United States Patent
Willis et al.

(10) Patent No.: US 8,143,261 B2
(45) Date of Patent: *Mar. 27, 2012

(54) THIAZOLO (4,5-D) PYRIMIDINE COMPOUNDS

(75) Inventors: Paul Andrew Willis, Loughborough (GB); Roger Bonnert, Loughborough (GB); Simon Fraser Hunt, Loughborough (GB); Iain Alistair Stewart Walters, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 158 days.

This patent is subject to a terminal disclaimer.

(21) Appl. No.: 12/432,224

(22) Filed: Apr. 29, 2009

(65) Prior Publication Data

US 2009/0281123 A1   Nov. 12, 2009

Related U.S. Application Data

(63) Continuation of application No. 10/863,995, filed on Jun. 9, 2004, now abandoned, which is a continuation of application No. 10/089,571, filed as application No. PCT/GB00/03692 on Sep. 26, 2000, now Pat. No. 6,790,850.

(30) Foreign Application Priority Data

Oct. 1, 1999 (SE) ....................................... 9903544

(51) Int. Cl.
*A61K 31/519* (2006.01)
*C07D 513/04* (2006.01)

(52) U.S. Cl. .................................... 514/260.1; 544/255

(58) Field of Classification Search .................. 544/255; 514/260.1
See application file for complete search history.

(56) References Cited

U.S. PATENT DOCUMENTS

| | | | |
|---|---|---|---|
| 2,924,472 A | 2/1960 | Bush | |
| 3,182,062 A | 5/1965 | Pachter et al. | |
| 3,318,900 A | 5/1967 | Janssen | |
| 3,445,120 A | 5/1969 | Barr | |
| 4,061,459 A | 12/1977 | Parmann | |
| 4,126,689 A | 11/1978 | Sanczuk et al. | |
| 4,188,040 A | 2/1980 | Wolf et al. | |
| 4,213,619 A | 7/1980 | Arlt et al. | |
| 4,234,199 A | 11/1980 | Moncaster et al. | |
| 4,278,677 A | 7/1981 | Nedelec et al. | |
| 4,410,528 A | 10/1983 | Teranishi et al. | |
| 4,483,544 A | 11/1984 | Faerber et al. | |
| 4,641,858 A | 2/1987 | Roux | |
| 5,064,207 A | 11/1991 | Bengtsson | |
| 5,169,161 A | 12/1992 | Jones | |
| 5,297,824 A | 3/1994 | Imhof et al. | |
| 5,521,197 A | 5/1996 | Audia | |
| 5,599,028 A | 2/1997 | Neumann et al. | |
| 5,826,887 A | 10/1998 | Neumann et al. | |
| 5,988,695 A | 11/1999 | Corbett, Jr. | |
| 6,142,484 A | 11/2000 | Valls, Jr. | |
| 6,172,067 B1 | 1/2001 | Ito et al. | |
| 6,248,755 B1 | 6/2001 | Chapman et al. | |
| 6,329,381 B1 | 12/2001 | Kurimoto et al. | |
| 6,407,121 B1 | 6/2002 | Nagamine et al. | |
| 6,432,981 B1 | 8/2002 | Finke et al. | |
| 6,790,850 B1 | 9/2004 | Willis et al. | |
| 6,790,854 B2 | 9/2004 | Tsushima et al. | |
| 6,875,868 B2 | 4/2005 | Bonnert et al. | |
| 6,949,643 B2 | 9/2005 | Bonnert | |
| 6,958,343 B2 | 10/2005 | Bonnert et al. | |
| 6,958,344 B2 | 10/2005 | Bonnert et al. | |
| 7,071,193 B2 | 7/2006 | Bonnert et al. | |
| 7,169,778 B2 | 1/2007 | Denny et al. | |
| 2003/0032642 A1 | 2/2003 | Bonnert et al. | |
| 2003/0107189 A1 | 6/2003 | Bonnert et al. | |
| 2003/0119869 A1 | 6/2003 | Burrows et al. | |
| 2004/0157853 A1 | 8/2004 | Bonnert | |
| 2004/0224961 A1 | 11/2004 | Willis et al. | |
| 2005/0171345 A1 | 8/2005 | Bonnert et al. | |
| 2005/0234077 A1 | 10/2005 | Bonnert et al. | |
| 2005/0272750 A1 | 12/2005 | Brough et al. | |
| 2006/0100221 A1 | 5/2006 | Bonnert | |
| 2006/0111569 A1 | 5/2006 | Bonnert | |
| 2007/0142352 A1 | 6/2007 | Bonnert et al. | |
| 2007/0282103 A1 | 12/2007 | Butters et al. | |
| 2008/0306262 A1 | 12/2008 | Bonnert | |
| 2009/0043097 A1 | 2/2009 | Butters et al. | |

FOREIGN PATENT DOCUMENTS

| | | |
|---|---|---|
| DE | 2331223 | 1/1974 |
| DE | 4119767 | 12/1992 |
| EP | 0293078 | 11/1988 |
| EP | 0447324 | 9/1991 |
| EP | 0778277 | 6/1997 |
| EP | 1069124 | 1/2001 |
| EP | 1122257 | 8/2001 |
| EP | 1348709 | 10/2003 |
| GB | 1009477 | 11/1965 |
| GB | 2359079 | 8/2001 |
| JP | 51-88994 | 7/1993 |

(Continued)

OTHER PUBLICATIONS

Ahmed et al., "Novel synthesis of 1-aryl-9-alkyl-2,3,3a,4,9,9a-hexahydro-1H-pyrrolo[2,3-b]quinoxalines by lithium aluminum hydride reduction of N-phenyl-1-benzimidazolylsuccinimides", CAPLUS 79:92106 (1973) abstract.
Baly et al., "Biological Assays for C-X-C Chemokines", *Methods in Enzymology* 287:69-88 (1997).
Baxter et al., "Hit-to-Lead Studies: The Discovery of Potent, Orally Bioavailable Thiazolopyrimidine CXCR2 Receptor Antagonists", *Bioorg. Med. Chem. Lett.* 16(4):90-963 (2006).
Berge et al., "Pharmaceutical Salts", *J. Pharm. Sci.* 66:1-19 (1977).
Bodor et al., "Chemical Approaches to Drug Delivery", in: *Encyclopedia of Controlled Drug Delivery* (1999 ed.), pp. 285-298.

(Continued)

*Primary Examiner* — Susanna Moore

(74) *Attorney, Agent, or Firm* — Fish & Richardson P.C.

(57) ABSTRACT

The invention provides certain thiazolopyrimidine compounds of formula (I) or a pharmaceutically acceptable salt or solvate thereof, processes and intermediates used in their preparation, pharmaceutical compositions containing them and their use in therapy.

4 Claims, No Drawings

FOREIGN PATENT DOCUMENTS

| | | |
|---|---|---|
| WO | WO 97/22596 | 6/1997 |
| WO | WO 97/30035 | 8/1997 |
| WO | WO 97/32856 | 9/1997 |
| WO | WO 97/40035 | 10/1997 |
| WO | WO 98/08847 | 3/1998 |
| WO | WO 98/13354 | 4/1998 |
| WO | WO 98/25617 | 6/1998 |
| WO | WO 99/02166 | 1/1999 |
| WO | WO 99/04794 | 2/1999 |
| WO | WO 99/17773 | 4/1999 |
| WO | WO 99/36421 | 7/1999 |
| WO | WO 99/51608 | 10/1999 |
| WO | WO 00/08013 | 2/2000 |
| WO | WO 00/09511 | 2/2000 |
| WO | WO 00/38680 | 7/2000 |
| WO | WO 00/39129 | 7/2000 |
| WO | WO 00/40529 | 7/2000 |
| WO | WO 00/41669 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 01/25242 | 4/2001 |
| WO | WO 01/58902 | 8/2001 |
| WO | WO 01/58906 | 8/2001 |
| WO | WO 01/66525 | 9/2001 |
| WO | WO 01/92224 | 12/2001 |
| WO | WO 02/04434 | 1/2002 |
| WO | WO 02/08213 | 1/2002 |
| WO | WO 02/083693 | 10/2002 |
| WO | WO 03/024966 | 3/2003 |
| WO | WO 2004/026835 | 1/2004 |
| WO | WO 2004/026880 | 4/2004 |
| WO | WO 2005/033115 | 4/2005 |
| WO | WO 2005/056563 | 6/2005 |
| WO | WO 2005/082865 | 9/2005 |
| WO | WO 2006/064228 | 6/2006 |

OTHER PUBLICATIONS

CAPLUS, Accession No. 2000:76301, Document No. 132:98128, "Antiinflammatory and analgesic capsules containing betamethasone, vitamin B6, dihydrochlorothiazide and triamterene", 1998.
Chemcats, Accession No. 2001:1442861, "4, 7-Pteridinediamine, 9-phenyl-2-[(phenylmethyl)thio]-," CAS Registry 343347-55-7 (Jul. 1, 2001).
Chemical Abstracts, vol. 54, No. 10, May 1960, Abstract No. 9933f, C. Wayne Noell and Roland K. Robins, "Potential Purine Antagonists XVII. Synthesis of 2-methyl and 2-methylthio-6, 8-disubstituted purines", see formula III when R-SMe, R1=Cl, R2=OH.
Cohen et al., "Cytokine function: A study in biologic diversity", CAPLUS 125:31527 (1996).
Cowley et al., "Preparation of 1-(3-phenyloxypropyl)piperdine derivatives as opioid receptor ligands", CAPLUS 138:39189 (2002).
Faubl, "Preparation of 5-Tetrazolyl Groups from Carboxylic Acids. A Sequence Amenable to Sensitive Substrates", *Tetrahedron Letters* 6:491-494 (1979).
Finke et al., "Preparation of piperidinylmethylcyclopentanes as modulators of CCR-5 and/or CCR-3 chemokine receptors", CAPLUS 134:56576 (2000) CAS Listing, 77 answers.
Fukuda et al., "Preparation of benzotriazole derivatives as cardiovascular agents and antipsychotics", CAPLUS 123:340149 (1995).
Gavezzotti, "Are Crystal Structures Predictable?", *Acc. Chem. Res.* 27:309-314 (1994).
Gewald et al., "New Synthesis of Substituted 4-Amino-quinazolines and Their Heteroanaloga", *J. prakt. Chem.* 338:206-213 (1996).
Grant, "University of Minnesota—Twin Cities Campus College of Pharmacy, Annual Report", [online] 1999, [retrieve on Feb. 13, 2003]. Retrieved from the internet, http://www.msi.umn.edu/general/Reports/ar99/departments/pharmacy.html.

Grohe et al., "Cycloacylation of Enamines, I.—Synthesis of 2-Thiazolone Derivatives", *Liebigs Ann. Chem.* 1018-1024 (1973).
Kiriasis et al., "Synthesis and Properties of New Pteridine Nucleosides", *Dev. Biochem.* 4:49-53 (1978).
Lee et al., "Characterization of Two High Affinity Human Interleukin-8 Receptors", *J. Biol. Chem.* 267:16283-16287 (1992).
McNaught et al., "IUPAC Compendium of Chemical Terminology, $2^{nd}$ Ed" (1997), Blackwell Science.
Merritt et al., "Use of fluo-3 to measure cytosolic $Ca^{2+}$ in platelets and neutrophils: Loading cells with the dye, calibration of traces, measurements in the presence of plasma, and buffering of cytosolic $Ca^{2+}$", *Biochem. J.* 269:513-519 (1990).
Murdoch and Finn, "Chemokine receptors and their role in inflammation and infectious diseases", *Blood* 95:3032 (3043 (2000).
Nagahara et al., "Thiazolo[4,5-*d*]pyrimidine Nucleosides. The Synthesis of Certain 3-β-D-Ribofuranosylthiazolo(4,5-*d*]pyrimidines as Potential Immunotherapeutic Agents", *J. Med. Chem.* 33:407-415 (1990).
Ott et al., "4-amino-7, 8-dihydro-2-(methylmercapto)-8-β, -D-ribofuranosylpteridin-7-One. Modified Fusion Reaction with Trimethylsilylated Pteridine Derivatives", *Nucl. Acid. Chem.* 2:735-739 (1978).
Ott et al., "Zur Synthese des 4-Amino-7-oxo-7, 8-dihydropteridin-N-8-β-D-ribofuranosids—ein strukturanaloges Nucleosid des Adenosins", *Chem.Ber.* 107:339-361 (1974).
Pachter and Nemeth, "Pteridines. I. Synthesis of Some 6-Alkyl-7-aminopteridines from Nitrosopyrimidines", *J. Org. Chem.* 28:1187-1191 (1963).
Patent Abstracts of Japan, abstract of JP-5-202047 A (Chugai Pharmaceut. Co. Ltd.) Aug. 10, 1993.
Power et al., "Differential Histopathology and Chemokine Gene Expression in Lung Tissues following Respiratory Syncytial Virus (RSV) Challenge of Formalin-Inactivated RSV- or BBG2Na-Immunized Mice", *J. Virol.* 75:12421-12430 (2001).
Sato et al., "Psychotropic Agents. 3. 4-(4-Substituted piperidinyl)-1-(4-flurophenyl)-1-butanones with Potent Neuroleptic Activity," *Journal of Medicinal Chemistry* 21(11):1116-1120 (1978).
Souillac et al., "Characterization of Delivery Systems, Differential Scanning Calorimetry", in: *Encyclopedia of Controlled Drug Delivery* (1999 ed.), pp. 212-227.
Spickett and Timmis, "The Synthesis of Compounds with Potential Anti-folic Acid Activity. Part I. 7-Amino- and 7-Hydroxy-pteridines", *J. Chem. Soc.* pp. 2887-2895 (1954).
Taylor et al., "Molecular Determinants for Recognition of RU 24969 Analogs at Central 5-Hydroxytryptamine Recognition Sites: Use of a Bilinear Function and Substituent Volumes to Describe Steric Fit," *Molecular Pharmacology* 32:42-53 (1988).
Teranishi et al., "Piperidine derivatives and pharmaceutical compositions containing them", CAPLUS 95:132947 (1981).
Traves et al., "Specific CXC but not CC chemokines cause elevated monocyte migration in COPD: a role for $CXCR_2$", *Journal of Leukocyte Biology* 76:441-450 (2004).
Trivedi et al., "Section IV. Immunology, Endocrinology and Metabolic Diseases", *Annual Reports in Medicinal Chemistry* 35:191-200 (2000).
Vandenberk et al., "1-(Benzazolylalkyl)piperidines and their salts with acids", CAPLUS 87:23274 (1977).
Vartanyan et al., "Synthesis and biological activity of 1-substituted benzimidazole and benztriazole derivatives", CAPLUS 98:4503 (1983).
Vippagunta et al., "Crystalline Solids", *Advanced Drug Delivery Reviews* 48:3-26 (2001).
Weinstock et al., "Pteridines. XII. Structure-Activity Relationships of Some Pteridine Diuretics", *J. Med. Chem.* 11(3):573-579 (1968).
West, "Solid State Chemistry and its applications", Wiley, New York, pp. 358 & 365 (1988).
Wu et al., "Synthesis of Furanonaphthoquinones with Hydroxyamino Side Chains", *J. Nat. Prod.* 62:963-968 (1999).
Sato et al., "Psychotropic agents. 3. 4-(4-Substituted pipendinyl)-1-(4-flurophenyl)-1-butanones with potent neuroleptic activity", CAPLUS 89:208915 (1978).

THIAZOLO (4,5-D) PYRIMIDINE COMPOUNDS

CROSS-REFERENCE TO RELATED APPLICATIONS

This application is a continuation application under 35 U.S.C. §120 of and claims priority to U.S. application Ser. No. 10/863,995, filed Jun. 9, 2004 now abandoned, which is a continuation application under 35 U.S.C. §120 of and claims priority to U.S. Ser. No. 10/089,571, filed Mar. 29, 2002, now U.S. Pat. No. 6,790,850, which is a national stage application under 35 U.S.C. §371 of PCT International Application No. PCT/GB00/03692, filed Sep. 26, 2000, which claims priority to Swedish Application Serial No. 9903544-6, filed Oct. 1, 1999, all of which are incorporated in their entireties herein.

The present invention relates to certain thiazolopyrimidinone compounds, processes and intermediates used in their preparation, pharmaceutical compositions containing them and their use in therapy.

WO 98/08847 and EP0778277 each disclose a series of 6,5-hetero bicyclic compounds said to be useful as CRF antagonists.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1 a and 1 (3 (MIP-1 a and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3, CXCR4 and CX3CR1. These receptors represent good targets for drug development since agents which modulate these receptors would be useful in the treatment of disorders and diseases such as those mentioned above.

In accordance with the present invention, there is therefore provided a compound of formula (I) or a pharmaceutically acceptable salt or solvate thereof:

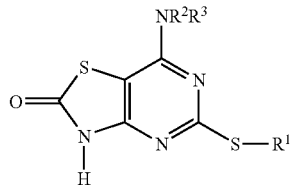

(I)

in which $R^1$ represents a $C_3$-$C_7$ carbocyclic, $C_1$-$C_8$ alkyl, $C_2$-$C_6$ alkenyl or $C_2$-$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or an aryl or heteroaryl group, both of which may be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$-$C_6$ alkyl or trifluoromethyl groups;

$R^2$ and $R^3$ each independently represent a hydrogen atom, or a $C_3$-$C_7$ carbocyclic, $C_1$-$C_8$ alkyl, $C_2$-$C_6$ alkenyl or $C_2$-$C_6$ alkynyl group, the latter four groups may be optionally substituted by one or more substituent groups independently selected from:

(a) halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$;

(b) a 3-8 membered ring optionally containing one or more atoms selected from O, S, $NR^8$ and itself optionally substituted by $C_1$-$C_3$-alkyl or halogen; or (c) an aryl group or heteroaryl group each of which may be optionally substituted by one or more substituents independently selected from halogen atoms, cyano, nitro, —$OR^4$, —$NR^5R^6$, —$CONR^5R^6$, —$NR^8COR^9$, —$SO_2NR^5R^6$, —$NR^8SO_2R^9$, $C_1$-$C_6$ alkyl and trifluoromethyl groups;

$R^4$ represents hydrogen, $C_1$-$C_6$ alkyl or a phenyl group the latter two of which may be optionally substituted by one or more substituent groups independently selected from halogen atoms, phenyl, —$OR^{11}$ and —$NR^{12}R^{13}$ $R^5$ and $R^6$ independently represent a hydrogen atom or a $C_1$-$C_6$ alkyl or phenyl group the latter two of which may be optionally substituted by one or more substituent groups independently selected from halogen atoms, phenyl, —$OR^{14}$ and —$NR^{15}R^{16}$, —$CONR^{15}R^{16}$, —$NR^{15}COR^{16}$, —$SONR^{15}R^{16}$, $NR^{15}SO_2R^{16}$ or $R^5$ and $R^6$ together with the nitrogen atom to which they are attached form a 4- to 7-membered saturated heterocyclic ring system optionally containing a further heteroatom selected from oxygen and nitrogen atoms, which ring system may be optionally substituted by one or more substituent groups independently selected from phenyl, —$OR^{14}$, —$COOR^{14}$, —$NR^{15}R^{16}$, —$CONR^{15}R^{16}$, —$NR^{15}COR^{16}$, —$SONR^{15}R^{16}$, $NR^{15}SO_2R^{16}$ or $C_1$-$C_6$ alkyl, itself optionally substituted by one or more substituents independently selected from halogen atoms and —$NR^{15}R^{16}$ and —$OR^{17}$ groups;

$R^{10}$ represents a hydrogen atom or a $C_1$-$C_6$-alkyl or a phenyl group, the latter two of which may be optionally substituted by one or more substituent groups independently selected from halogen atoms, phenyl, —$OR^{17}$ and —$NR^{15}R^{16}$; and each of $R^7$, $R^8$, $R^9$, $R^{11}$, $R^{12}$, $R^{13}$, $R^{14}R^{15}$, $R^{16}$, $R^{17}$ independently represents a hydrogen atom or a $C_1$-$C_6$, alkyl or a phenyl group.

In the context of the present specification, unless otherwise indicated, an alkyl or alkenyl group or an alkyl or alkenyl moiety in a substituent group may be linear or branched. Aryl groups include phenyl and naphthyl. Heteroaryl groups include 5- or 6-membered aromatic rings containing one or more heteroatoms selected from N, S, O. Examples include pyridine, pyrimidine, thiazole, oxazole, pyrazole, imidazole, furan.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

In formula (I) above, the group $R^1$ represents a $C_3$-$C_7$ carbocyclic, $C_1$-$C_8$ alkyl, $C_2$-$C_6$ alkenyl or $C_2$-$C_6$ alkynyl group, each of the groups being optionally substituted by one or more substituent groups independently selected from halogen atoms, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$ or an aryl or heteroaryl group, both of which may be optionally substituted by one or more substituents independently selected from halogen atoms, cyano, nitro, —$OR^4$, —$NR^5R^6$, —$CONR^5R^6$, —$COOR^7$, —$NR^8COR^9$, —$SR^{10}$, —$SO_2R^{10}$, —$SO_2NR^5R^6$, —$NR^8SO_2R^9$, $C_1$-$C_6$ alkyl or trifluoromethyl groups. Particularly advantageous compounds of formula (I) are those in which $R^1$ represents an optionally substituted benzyl group. More preferably $R^1$ represents benzyl or benzyl substituted by one or more $C_1$-$C_6$ alkyl, $C_1$-$C_6$ alkoxy or halogen atoms.

When $R^2$ and $R^3$ represent a group substituted by one or more 3-8 membered rings optionally containing one or more atoms selected from O, S or $NR^8$, examples of such groups include piperidine, pyrrolidine, piperazine and morpholine.

Preferably one of $R^2$ and $R^3$ is hydrogen and the other is $C_1$-$C_8$ alkyl substituted by hydroxy and one or more methyl or ethyl groups. More preferably one of $R^2$ and $R^3$ is hydrogen and the other is $CH(CH_3)CH_2OH$, $CH(Et)CH_2OH$, $C(CH_3)_2CH_2OH$ or $CH(CH_2OH)_2$. When one of $R^2$ and $R^3$ is hydrogen and the other is $CH(CH_3)CH_2OH$ or $CH(Et)CH_2OH$ the resulting compounds of formula (I) are preferably in the form of the (R) isomer.

Particularly preferred compounds of the invention include:
7-[(2-Hydroxy-1,1-dimethylethyl)amino]-5-[(phenylmethyl)thio]thiazolo[4,5-d]pyrimidin-2(3H)-one,
(R)-7-[[1-Hydroxymethyl)propyl]amino]-5-[(phenylmethyl)thio]thiazolo[4,5-d]pyrimidin-2(3H)-one,
(R)-7-[(2-Hydroxy-1-methylethyl)amino]-5-[(phenylmethyl)thio]thiazolo[4,5-d]pyrimidin-2(3H)-one,
5-[[(2,3-Difluorophenyl)methyl]thio]-7-[(2-hydroxy-1,1-dimethylethyl)amino]thiazolo[4,5d]pyrimidin-2(3H)-one,
5-[[(2,3-Difluorophenyl)methyl]thio]-7-[[(1R)-2-hydroxy-1-methylethyl]amino]thiazolo[4,5-d]pyrimidin-2(3H)-one,
5-[[(2,3-difluorophenyl)methyl]thio]-7-[[2-hydroxyethoxy)ethyl]amino]thiazolo[4,5-d]pyrimidin-2(3H)-one,
5-[[(2,3-difluorophenyl)methyl]thio]-7-[[2-hydroxy-1-(hydroxymethyl)ethyl]amino]thiazolo[4,5-d]pyrimidin-2(3H)-one,
7-[(2-aminoethyl)amino]-5-[[(2,3-difluorophenyl)methyl]thio]thiazolo[4,5-d]pyrimidin-2(3H)-one,
5-[[(2,3-difluorophenyl)methyl]thio]-7-[(2-hydroxyethyl)amino]thiazolo[4,5-d]pyrimidin-2(3H)-one,
N-[2-[[5-[[(2,3-difluorophenyl)methyl]thio]-2,3-dihydro-2-oxothiazolo[4,5-d]pyrimidin-7-yl]amino]ethyl]methanesulfonamide,
(+/−)-5-[[(2,3-difluorophenyl)methyl]thio]-7-[[2-(2-hydroxyethoxy)-1-methylethyl]amino]thiazolo[4,5-d]pyrimidin-2(3H)-one,
7-[[(1R)-2-amino-1-methylethyl]amino]-5-[[(2,3-difluorophenyl)methyl]thio]thiazolo[4,5-d]pyrimidin-2(3H)-one,
5-[[(2,3-difluorophenyl)methyl]thio]-7-[[(1R)-2-[(2-hydroxyethyl)amino]-1-methylethyl]amino]thiazolo[4,5-d]pyrimidin-2(3H)-one,
5-[[(2,3-difluorophenyl)methyl]thio]-7-[[(1R)-2-dimethylamino)-1-methylethyl]amino]thiazolo[4,5-d]pyrimidin-2(3H)-one,
5-[[[4-(2-aminoethoxy)-3-chlorophenyl]methyl]thio]-7-[[(1R)-2-hydroxy-1-methylethyl]amino]thiazolo[4,5-d]pyrimidin-2(3H)-one,
5-[[3-Chloro-4-methoxyphenyl)methyl]thio]-7-[[(1R)-2-hydroxy-1-methylethyl]amino]thiazolo[4,5-d]pyrimidin-2(3H)-one,
5-[[3-Chloro-2-fluorophenyl)methyl]thio]-7-[[(1R)-2-hydroxy-1-methylethyl]amino]thiazolo[4,5-d]pyrimidin-2(3H)-one,
5-[[(2,3-Difluorophenyl)methyl]thio]-7-[[(3R,4R)-4-hydroxypyrrolidin-3-yl]amino]-thiazolo[4,5-d]pyrimidin-2(3H)-one,
5-[[(2,3-Difluorophenyl)methyl]thio]-7-[(3R)-pyrrolidin-3-ylamino]thiazolo[4,5-d]pyrimidin-2(3H)-one,
7-[[(1R)-2-Hydroxy-1-methylethyl]-amino]-5-[[(2-methyl-4-thiazolyl)methyl]thio]thiazolo[4,5-d]pyrimidin-2(3H)-one,
7-[[2-Hydroxy-1-(hydroxymethyl)ethyl]amino]-5-[[(2-methyl-4-thiazolyl)methyl]thio]thiazolo[4,5-d]pyrimidin-2(3H)-one,
7-[(2-Hydroxy-1,1-dimethylethyl)amino]-5-[[(2-methyl-4-thiazolyl)methyl]thio]thiazolo[4,5-d]pyrimidin-2(3H)-one,
7-[(2-Hydroxy-1,1-dimethylethyl)amino]-5-[[(2-methylphenyl)methyl]thio]thiazolo[4,5-d]pyrimidin-2(3H)-one,
5-[(2-Furanylmethyl)thio]-7-[[(1R)-2-hydroxy-1-methylethyl]amino]thiazolo[4,5-d]pyrimidin-2(3H)-one,
7-[[(1R)-2-Amino-1-methylethyl]amino]-5-[[(3-chloro-2-fluorophenyl)methyl]thio]thiazolo[4,5-d]pyrimidin-2(3H)-one
(2S)-2-[[5-[[(2,3-Difluorophenyl)methyl]thio]-2,3-dihydro-2-oxothiazolo[4,5-d]pyrimidin-7-yl]amino]-3-hydroxypropanamide,
7-[[(1R)-2-hydroxy-1-methylethyl]amino]-5-[(2-thienylmethyl)thio]thiazolo[4,5-d]pyrimidin-2(3H)-one,
7-[[(1R)-2-hydroxy-1-methylethyl]amino]-5[[[3-methyl-4-(methylsulfonyl)phenyl]methyl]thio]thiazolo[4,5-d]pyrimidin-2(3H)-one,
5-[[[3-chloro-4-(trifluoromethoxy)phenyl]methyl]thio]-7-[[(1R)-2-hydroxy-1-methylethyl]amino]thiazolo[4,5-d]pyrimidin-2(3)-one,
5-[[[2-fluoro-3-(trifluoromethyl)phenyl]methyl]thio]-7-[[(1R)-2-hydroxy-1-methylethyl]amino]thiazolo[4,5-d]pyrimidin-2(3)-one,
5-[[(2,3-difluorophenyl)methyl]thio]-7-[2-[(dimethylamino)ethyl]amino]thiazolo[4,5-d]pyrimidin-2(3H)-one,
5-[[(2-fluorophenyl)methyl]thio]-7-[[(1R)-2-hydroxy-1-methylethyl]amino]thiazolo[4,5-d]pyrimidin-2(3H)-one,
7-[[(1R)-2-hydroxy-1-methylethyl]amino]-5-[[(2-methoxyphenyl)methyl]thio]thiazolo[4,5-d]pyrimidin-2(3H)-one,
7-[[(1R)-2-hydroxy-1-methylethyl]amino]-5-[(2-phenoxyethyl)thio]thiazolo[4,5-d]pyrimidin-2(3H)-one,
7-[[(1R)-2-hydroxy-1-methylethyl]amino]-5-[[(3-methylphenyl)methyl]thio]thiazolo[4,5-d]pyrimidin-2(3H)-one,
5-[[(2-fluoro-3-methylphenyl)methyl]thio]-7-[[(1R)-2-hydroxy-1-methylethyl]amino]thiazolo[4,5-d]pyrimidin-2(3H)-one,
5-[[(3-chlorophenyl)methyl]thio]-7-[[(1R)-2-hydroxy-1-methylethyl]amino]thiazolo[4,5-d]pyrimidin-2(3H)-one,
5-[[(3-bromophenyl)methyl]thio]-7-[[(1R)-2-hydroxy-1-methylethyl]amino]thiazolo[4,5-d]pyrimidin-2(3H)-one,
5-[[[4-(difluoromethoxy)phenyl]methyl]thio]-7-[[(1R)-2-hydroxy-1-methylethyl]amino]thiazolo[4,5-d]pyrimidin-2(3H)-one, (+/−)-5-[[(2,3-difluorophenyl)methyl]thio]-7-[[2-hydroxy-1-(methoxymethyl)ethyl]amino]thiazolo[4,5-d]pyrimidin-2(3H)-one, 7-[[2-hydroxy-1-(hydroxymethyl)ethyl]amino]-5-[(phenylmethyl)thio]thiazolo[4,5-d]pyrimidin-2(3H)-one, 5-[[(2-bromophenyl)methyl]thio]-7-[[(1R)-2-hydroxy-1-methylethyl]amino]thiazolo[4,5-d]pyrimidin-2(3H)-one, 5-[[(2,3-Difluorophenyl)methyl]thio]-7-[[(1R)-2-hydroxy-1-methylethyl]amino]thiazolo[4,5-d]pyrimidin-2(3H)-one, 5-[[3-Chloro-2-fluorophenyl)methyl]thio]-7-[[(1R)-2-hydroxy-1-methylethyl]amino]thiazolo[4,5-d]pyrimidin-2(3H)-one, (+/−)-5-[[(2,3-difluorophenyl)methyl]thio]-7-[[2-hydroxy-1-(methoxymethyl)ethyl]amino]thiazolo[4,5-d]pyrimidin-2(3H)-one, 7-[[2-hydroxy-1-(hydroxymethyl)ethyl]amino]-5-[(phenylmethyl)thio]thiazolo[4,5-d]pyrimidin-2(3H)-one, 7-[[(1R)-2-Hydroxy-1-methylethyl]amino]-5-[(phenylmethyl)thio]thiazolo[4,5-d]pyrimidin-2(3H)-one, 5-[(5-chloro-1,2,3-thiadiazol-4-yl)thio]-7-[[(1R)-2-hydroxy-1-methylethyl]amino]-thiazolo[4,5-d]pyrimidin-2(3H)-one, and their pharmaceutically acceptable salts and solvates.

Particular salts of compounds of formula (I) include:

5-[[(2,3-Difluorophenyl)methyl]thio]-7-[[(1R)-2-hydroxy-1-methylethyl]amino]thiazolo[4,5-d]pyrimidin-2(3H)-one sodium salt, 5-[[3-Chloro-2-fluorophenyl)methyl]thio]-7-[[(1R)-2-hydroxy-1-methylethyl]amino]thiazolo[4,5-d]pyrimidin-2(3H)-one sodium salt, (+/−)-5-[[(2,3-difluorophenyl)methyl]thio]-7-[[2-hydroxy-1-(methoxymethyl)ethyl]amino]thiazolo[4,5-d]pyrimidin-2(3H)-one sodium salt, 7-[[2-hydroxy-1-(hydroxymethyl)ethyl]amino]-5-[(phenylmethyl)thio]thiazolo[4,5-d]pyrimidin-2(3H)-one sodium salt, or 7-[[(1R)-2-Hydroxy-1-methylethyl]amino]-5-[(phenylmethyl)thio]thiazolo[4,5-d]pyrimidin-2(3H)-one sodium salt.

Further particular salts of compounds of formula (I) include:

7-[[(1R)-2-amino-1-methylethyl]amino]-5-[[(2,3-difluorophenyl)methyl]thio]thiazolo[4,5-d]pyrimidin-2(3H)-one trifluoroacetate, 5-[[(2,3-difluorophenyl)methyl]thio]-7-[[(1R)-2-[(2-hydroxyethyl)amino]-1-methylethyl]amino]thiazolo[4,5-d]pyrimidin-2(3H)-one trifluoroacetate, 5-[[(2,3-difluorophenyl)methyl]thio]-7-[[(1R)-2-(dimethylamino)-1-methylethyl]amino]thiazolo[4,5-d]pyrimidin-2(3H)-one, 5-[[[4-(2-aminoethoxy)-3-chlorophenyl]methyl]thio]-7-[[(1R)-2-hydroxy-1-methylethyl]amino]thiazolo[4,5-d]pyrimidin-2(3H)-one trifluoroacetate, 5-[[(2,3-difluorophenyl)methyl]thio]-7-[2-[(dimethylamino)ethyl]amino]thiazolo[4,5-d]pyrimidin-2(3H)-one monohydrochloride, or 5-[[(2,3-Difluorophenyl)methyl]thio]-7-[(3R)-pyrrolidin-3-ylamino]thiazolo[4,5-d]pyrimidin-2(3H)-one dihydrochloride.

According to the invention there is also provided a process for the preparation of a compound of formula (I) which comprises either:
Treatment of a Compound of Formula (IIA)

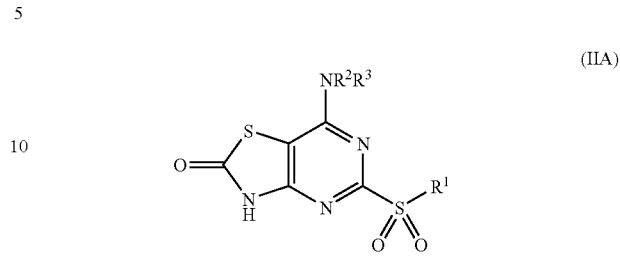

where $R^1$, $R^2$ and $R^3$ are as defined in formula (I) with a thiol $R^1SH$ in the presence of a suitable base and optionally forming a pharmaceutically acceptable salt. The reaction may be carried out in a mixed solvent of DMSO and ethanol at a temperature between 0° C. and 100° C. using sodium borohydride as the base.

Compounds of formula (IIA) where $R^1$, $R^2$ and $R^3$ are as defined in formula (I) may be prepared by treatment of compounds of formula (I) with a suitable oxidising agent such as oxone. The reaction may be carried out in a solvent such as acetonitrile at a temperature between 0° C. and 100° C.

Or Treatment of a Compound of Formula (IIB):

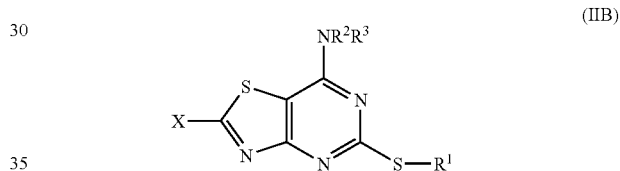

where $R^1$, $R^2$ and $R^3$ are as defined in formula (I) and X is a leaving group with a metal alkoxide, followed by treatment with an acid or base and optionally forming a pharmaceutically acceptable salt.

X is any suitable leaving group such as halogen. The reaction may be carried out in an alcohol solvent such as methanol and the deprotection carried out in a solvent such as 1,4-dioxane. Examples of metal alkoxides include potassium methoxide. Examples of suitable acids include hydrochloric acid. Preferably the compound of formula (IIB) is treated with a metal alkoxide such as potassium methoxide followed by an acid such as conc. HCl in a solvent such as 1,4-dioxane.

Compounds of formula (IIB) where $R^1$, $R^2$ and $R^3$ are as defined in formula (I) and X is a halogen, may be prepared from corresponding compounds (IIB) where $R^1$, $R^2$ and $R^3$ are as defined in formula (I) and X is $NH_2$ by treatment with a diazotizing agent such as isoamylnitrite and a halogenating agent such as bromoform.

Compounds of formula (IIB) where $R^1$, $R^2$ and $R^3$ are as defined in formula (I) and X is $NH_2$ may be prepared either by treatment of a compound of formula (IIIA):

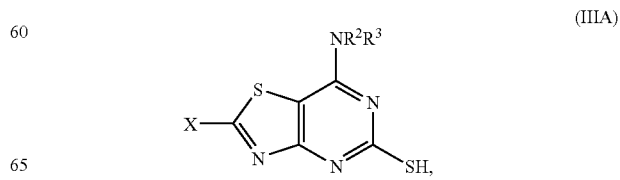

where $R^2$ and $R^3$ are as defined in formula (I) and X is $NH_2$ with a compound of formula $R^1X$ where $R^1$ is as defined above and X is a leaving group such as bromide in the presence of a base such as diisopropylethylamine in an inert solvent such as DMSO/N-methylpyrrolidinone at a temperature between 0° C. and 100° C.

Compounds of formula (IIIA) where $R^2$ and $R^3$ are as defined in formula (I) and X is $NH_2$ may be prepared by treatment of a compound of formula (IIB) where $R^2$ and $R^3$ are as defined in formula (I), X is $NH_2$ and $R^1$ is a suitable benzyl group such as benzyl or 2,3-difluorobenzyl with a reducing medium such as sodium metal in liquid ammonia, or by treatment of a compound of formula (IIIB):

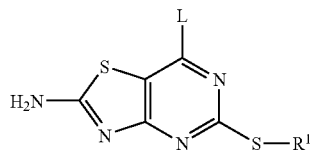

(IIIB)

where $R^1$ is as defined in formula (I) and L is a leaving group such as chlorine with an amine $HNR^2R^3$ where $R^2$ and $R^3$ are as defined in formula (I). The reaction may be carried out in a solvent such as N-methyl-pyrrolidine at a temperature between 0° C. and 150° C.

Compounds of formula (IIIB) where $R^1$ is as defined in formula (I) and L is a halogen may be prepared by treating a compound of formula (III) where $R^1$ is as defined in formula (I) and L is a hydroxyl group with a halogenating agent such as phosphorous oxychloride. The reaction may be carried out in the presence of dimethylaniline at reflux.

Compounds of formula (IIIB) where $R^1$ is as defined in formula (I) and L is a hydroxyl group may be formed either by treatment of a compound of formula (IVA) with a compound of formula $R^1X$ where $R^1$ is as defined above and X is a leaving group such as bromide in the presence of a base such as potassium tert-butoxide in an inert solvent such as DMSO at ambient temperature.

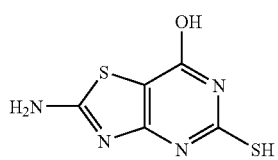

(IVA)

Or by heating a compound of formula (IVB) where $R^1$ is as defined above.

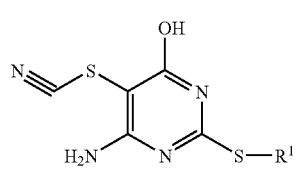

(IVB)

The reaction is preferably carried out in a suitable solvent such as DMF at elevated temperature, for example at about 120° C.

Compounds of formula (IVB) may be readily prepared by reacting a compound of general formula (V) wherein $R^1$ is as defined above, with potassium thiocyanate and bromine in an inert solvent such as dimethylformamide/pyridine.

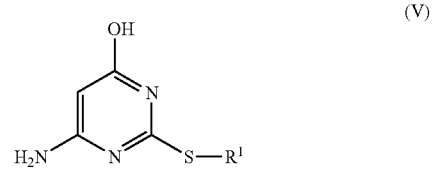

(V)

Compounds of formula (V) are suitably prepared by reacting a compound of formula (VI):

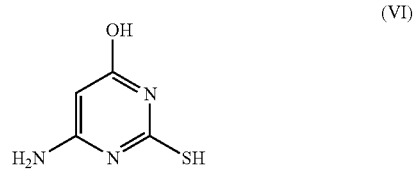

(VI)

with a compound of formula $R^1X$ where $R^1$ is as defined above and X is a leaving group such as bromide in the presence of a base such as sodium hydride in an inert solvent such as DMF at ambient temperature.

Compounds of formula (IVA) and (VI) are either commercially available or are well known in the literature.

It will be appreciated by those skilled in the art that in the processes described above the functional groups (e.g. hydroxyl groups) of intermediate compounds may need to be protected by protecting groups. The final stage in the preparation of the compounds of the invention may involve the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

Novel intermediate compounds form a further aspect of the invention. In particular compounds of formula (IIA), (IIB) and (IIIA) are novel and form an aspect of the invention.

The compounds of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate, or p-toluenesulphonate.

The compounds of formula (I) have activity as pharmaceuticals, in particular as modulators of chemokine receptors, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis, acute, allergic, atrophic rhinitis and chronic rhinitis including rhinitis caseosa, hypertrophic rhinitis, rhinitis purulenta, rhinitis sicca and rhinitis medicamertosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura; post-operative adhesions, and sepsis.

(6) (allograft rejection) acute and chronic following, for example, transplantation of kidney, heart, liver, lung, bone marrow, skin and cornea; and chronic graft versus host disease;

(7) Cancers, especially non-small cell lung cancer (NSCLC), malignant melanoma, prostate cancer and squamous sarcoma, and tumour metastasis;

(8) Diseases in which angiogenesis is associated, with raised CXCR-2 chemokine levels (e.g. NSCLC, diabetic retinopathy).

(9) Cystic fibrosis, stroke, re-perfusion injury in the heart, brain, peripheral limbs and other organs.

(10) Burn wounds & chronic skin ulcers

(11) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CXC chemokine receptor subfamily, more preferably the target chemokine receptor is the CXCR2 receptor, Particular conditions which can be treated with the compounds of the invention are psoriasis, diseases in which angiogenesis is associated with raised CXCR2 chemokine levels, and COPD. It is preferred that the compounds of the invention are used to treat psoriasis.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or, suspensions, or by subcutaneous administration or by rectal administration in the form of suppositories or transdermally. Preferably the compounds of the invention are administered orally.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on a Finnigan Mat SSQ7000 or Micromas Platform spectrometer. Where necessary, the reactions were performed under an inert atmosphere of either nitrogen or argon. Chromatography was generally performed using Matrex Silica 60® (35-70 micron) or Prolabo Silica gel 60® (35-70 micron) suitable for flash silica gel chromatography. High pressure liquid chromatography purification was performed using either a Waters Micromass LCZ with a Waters 600 pump controller, Waters 2487 detector and Gilson FC024 fraction collector or a Waters Delta Prep 4000. The abbreviations m.p. and DMSO used in the examples stand for melting point and dimethyl sulphoxide respectively.

EXAMPLE 1

7-[(2-Hydroxy-1,1-dimethylethyl)amino]-5-[(phenylmethyl)thio]thiazolo[4,5-d]pyrimidin-2(3H)-one (a) Thiocyanic acid, 6-amino-1,4-dihydro-4-oxo-2-[(phenylmethyl)thio]-5-pyrimidinyl ester 6-Amino-2-[(phenylmethyl)thio]-4(1H)-pyrimidinone (10.5 g)[preparation as described in WO 9635678] and potassium thiocyanate (25 g) in N,N-dimethylformamide (200 ml) were heated together at 65° C. Pyridine (6.3 ml) was added and the solution-cooled to 5° C. Bromine (2.2 ml) was added slowly and the reaction mixture stirred for 2 hours at 5-10° C. The reaction mixture was poured onto ice water, stirred for 1 hour and the solid was isolated by filtration. After washing with water and ether, a pure sample was obtained after trituration with hot methanol.

MS (APCI) 291 (M+H, 100%).

(b) 2-Amino-5-[(phenylmethyl)thio]thiazolo[4,5-d]pyrimidin-7(4H)-one

The product of example 1 step a) (7.35 g) was heated at 120° C. in N,N-dimethylformamide (40 ml)/water (10 ml) for 10 hours. After cooling, the resulting solid was filtered off, washed with water, then ethyl acetate to give the subtitle compound.

m.p. 325° C.
MS (APCI) 291 (M+H, 100%).

(c) 7-Chloro-5-[(phenylmethyl)thio]thiazolo[4,5-d]pyrimidin-2-amine

The product from example 1 step b) (0.89 g), phosphorus oxychloride (12 ml) and N,N-dimethylaniline (1.2 ml) were heated at reflux for 2 hours. The cooled reaction mixture was poured onto ice water and stirred for 2 hours. Chromatography (SiO$_2$, methanol/dichloromethane as eluant) gave the sub-title compound.

m.p. 217-218.5° C.
MS (APCI) 309 (M+H, 100%).

(d) 2-[[2-Amino-5-[(phenylmethyl)thio]thiazolo[4,5-d]pyrimidin-7-yl]amino]-2-methyl-1-propanol The product from example 1 step c) (0.6 g) and 1-amino-2-methyl-propan-2-ol (1.1 g) in tetrahydrofuran (10 ml) was heated in a sealed vessel at 100° C. for 18 hours. The mixture was evaporated to dryness and purified (SiO$_2$, ethyl acetate as eluant) to give the subtitle compound (0.46 g).

MS (APCI) 362 (M+H$^+$, 100%).

(e) 2-[[2-Bromo-5-[(phenylmethyl)thio]thiazolo[4,5-d]pyrimidin-7-yl]amino]-2-methyl-1-propanol To a solution of the product from example 1 step d) (0.1 g) in bromoform (5 ml) was added isoamylnitrite (0.13 ml) and the mixture heated at 60° C. for 10 mins. The mixture was evaporated to dryness and purified (SiO$_2$, ethyl acetate: dichloromethane 1:9 as eluant) to give the subtitle compound as a colourless solid (0.043 g).

MS (APCI) 427 (M+H$^+$, 100%).

(f) 2-[[2-Methoxy-5-[(phenylmethyl)thio]thiazolo[4,5-d]pyrimidin-7-yl]amino]-2-methyl-1-propanol To a solution of the product from example 1 step e) (0.36 g) in methanol (5 ml) was added potassium hydroxide (0.095 g) and the mixture stirred for 30 mins. The mixture was neutralised with concentrated hydrochloric acid then evaporated to dryness and purified (SiO$_2$, ethyl acetate:dichloromethane 1:9 as eluant) to give the subtitle compound as a colourless solid (0.245 g).

MS (APCI) 377 (M+H$^+$, 100%).

(g) 7-[(2-Hydroxy-1,1-dimethylethyl)amino]-5-[(phenylmethyl)thio]thiazolo[4,5-d]pyrimidin-2(3H)-one To a solution of the product from example 1 step f) (0.21 g) in 1,4-dioxane (5 ml) was added water (0.1 ml) and concentrated hydrochloric acid (1 drop). The mixture heated at 45° C. for 3 hours then evaporated to dryness. Recrystallisation (acetonitrile) gave the title compound (0.110 g).

M.P 207-8° C.
MS (APCI) 363 (M+H$^+$, 100%).
NMR δH (d$_6$-DMSO) 12.37 (1H, s), 7.43-7.23 (5H, m), 6.61 (H, bs), 4.81 (1H, t), 4.34 (2H, s), 3.55 (2H, bs), 1.32 (6H, s).

EXAMPLE 2

(R)-7-[[1-(Hydroxymethyl)propyl]amino]-5-[(phenylmethyl)thio]thiazolo[4,5-d]pyrimidin-2(3H)-one (a) (R)-2-[[2-Amino-5-[(phenylmethyl)thio]thiazolo[4,5-d]pyrimidin-7-yl]amino]-1-butanol To a mixture of the product of example 1 step c) (2.5 g) and (R)-(−)-2-amino-1-butanol (5 g) in a solvent of N-methylpyrrolidinone (10 ml) was added N,N-diisopropylethylamine (5 ml) and the resultant mixture heated at 100° C. for 10 hours. The mixture was poured into water and the product collected by filtration to give the subtitle compound (2.5 g)

MS (APCI) 362 (M+H$^+$, 100%).

(b) (R-2-[[2-Bromo-5-[(phenylmethyl)thio]thiazolo[4,5-d]pyrimidin-7-yl]amino]-1-butanol Prepared by the method of example 1 step e), using the product of example 2 step a).

MS (APCI) 427 (M+H$^+$, 100%).

(c) (R)-2-[[2-Methoxy-5-[(phenylmethyl)thio]thiazolo[4,5-d]pyrimidin-7-yl]amino]-1-butanol Prepared by the method of example 1 step f), using the product of example 2 step b).

MS (APCI) 377 (M+H$^+$, 100%).

(d) (R-7-[[1-(Hydroxmethyl)propyl]amino]-5-[(phenylmethyl)thio]thiazolo[4,5-d]pyrimidin-2(3H)-one Prepared by the method of example 1 step g), using the product of example 2 step c).

M.P 217-8° C.
MS (APCI) 363 (M+H$^+$, 100%).
NMR δH (d$_6$-DMSO) 12.37 (1H, s), 7.43-7.21 (6H, m), 4.68 (1H, t), 4.32 (2H, q), 4.09 (1H, bs), 3.47-3.32 (2H, m), 1.69-1.59 (1H, m), 1.48-1.41 (1H, m), 0.82 (3H, t).

EXAMPLE 3

(R)-7-[(2-Hydroxy-1-methylethyl)amino]-5-[(phenylmethyl)thio]thiazolo[4,5-d]pyrimidin-2(3H)-one (a) (R)-2-[[2-Amino-5-[(phenylmethyl)thio]thiazolo[4,5-d]pyrimidin-7-yl]amino]-1-propanol Prepared by the method of example 2 step a), using the product of example 1 step c) and (R)-(−)-2-amino-1-propanol.
MS (APCI) 412 (M+H$^+$, 100%).

(b) (R)-2-[[2-Bromo-5-[(phenylmethyl)thio]thiazolo[4,5-d]pyrimidin-7-yl]amino]-1-propanol Prepared by the method of example 1 step e), using the product of example 3 step a)
MS (APCI) 348 (M+H$^+$, 100%).

(c) (R)-2-[[2-Methoxy-5-[(phenylmethyl)thio]thiazolo[4,5-d]pyrimidin-7-yl]amino]-1-propanol Prepared by the method of example 1 step f), using the product of example 3 step b)
MS (APCI) 363 (M+H$^+$, 100%).

(d) (R)-7-[(2-Hydroxy-1-methylethyl)amino]-5-[(phenylmethyl)thio]thiazolo[4,5-d]pyrimidin-2(3H)-one Prepared by the method of example 1 step g), using the product of example 3 step c).
MS (APCI) 349 (M+H$^+$, 100%).
NMR δH (d$_6$-DMSO) 12.38 (1H, s), 7.44-7.20 (6H, m), 4.72 (1H, t), 4.32 (2H, m), 4.23 (1H, m), 3.49-3.29 (2H, m), 1.11 (3H, d).

EXAMPLE 4

5-[[(2,3-Difluorophenyl)methyl]thio]-7-[(2-hydroxy-1,1-dimethylethyl)amino]thiazolo[4,5-d]pyrimidin-2(3H)-one (a) 2-Amino-5-[[(2,3-difluorophenyl)methyl]thio]thiazolo[4,5-d]pyrimidin-7(4H)-one Potassium t-butoxide solution (0.45 ml of 1M solution in tetrahydrofuran) was added to a stirred solution of 2-amino-5,6-dihydro-5-thioxo-thiazolo[4,5-d]pyrimidin-7(4H)-one (0.09 g) [Cited: Indian J. Chem., Sect. B (1989), 28B(11), 964-5.] and 2,3-difluorobenzyl bromide in dimethyl sulphoxide (2 ml). After stirring for 3 days, the reaction mixture was poured onto water to give and the subtitle compound, isolated by filtration.
MS (APCI) 327 (M+H$^+$, 100%).

(b) 7-Chloro-5-[[(2,3-difluorophenyl)methyl]thio]thiazolo[4,5-d]pyrimidin-2-amine Prepared by the method of example 1 step c), using the product of example 4 step a).
MS (APCI) 345 (M+H$^+$, 100%).

(c) 2-[[2-Amino-5-[[(2,3-difluorophenyl)methyl]thio]thiazolo[4,5-d]pyrimidin-7-yl]amino]-2-methyl-1-propanol Prepared by the method of example 2 step a), using the product of example 4, step b) and 2-amino-2-methylpropanol.
MS (APCI) 398 (M+H$^+$, 100%).

(d) 2-[[2-Bromo-5-[[(2,3-difluorophenyl)methyl]thio]thiazolo[4,5-d]pyrimidin-7-yl]amino]-2-methyl-1-propanol Prepared by the method of example 1 step e), using the product of example 4 step c).
MS (APCI) 462 (M+H$^+$, 100%).

(e) 2-[[5-[[(2,3-Difluorophenyl)methyl]thio]-2-methoxythiazolo[4,5-d]pyrimidin-7-yl]amino]-2-methyl-1-propanol Prepared by the method of example 1 step f), using the product of example 4 step d).
MS (APCI) 413 (M+H$^+$, 100%).

(f) 5-[[(2,3-Difluorophenyl)methyl]thio]-7-[(2-hydroxy-1,1-dimethylethyl)amino]thiazolo[4,5-d]pyrimidin-2(3H)-one Prepared by the method of example 1 step f), using the product of example 4 step e).
MS (APCI) 399 (M+H$^+$, 100%).
NMR δH (d$_6$-DMSO) 12.41 (1H, s), 7.41-7.30 (2H, m), 7.21-7.13 (1H, m), 6.64 (1H, bs), 4.79 (1H, t), 4.41 (2H, s), 3.53 (2H, d), 1.29 (6H, s).

EXAMPLE 5

5-[[(2,3-Difluorophenyl)methyl]thio]-7-[[(1R)-2-hydroxy-1-methylethyl]amino]thiazolo[4,5-d]pyrimidin-2(3H)-one (a) (2R)-2-[[2-Amino-5-[[(2,3-difluorophenyl)methyl]thio]thiazolo[4,5-d]pyrimidin-7-yl]amino]-1-propanol Prepared by the method of example 2 step a), using the product of example 4 step b) and (R)-(−)-2-amino-1-propanol.
MS (APCI) 384 (M+H$^+$, 100%).

(b) (2R)-2-[[2-Bromo-5-[[(2,3-difluorophenyl)methyl]thio]thiazolo[4,5-d]pyrimidin-7-yl]amino]-1-propanol Prepared by the method of example 1 step e), using the product of example 5 step a).
MS (APCI) 448 (M+H$^+$, 100%).

(c) (2R)-2-[[5-[[(2,3-difluorophenyl)methyl]thio]-2-methoxythiazolo[4,5-d]pyrimidin-7-yl]amino]-1-propanol Prepared by the method of example 1 step f), using the product of example 5 step b)
MS (APCI) 398 (M+H$^+$, 100%).

(d) 5-[[(2,3-Difluorophenyl)methyl]thio]-7-[[(1R)-2-hydroxy-1-methylethyl]amino]thiazolo[4,5-d]pyrimidin-2(3H)-one Prepared by the method of example 1 step g), using the product of example 5 step c).
MS (APCI) 385 (M+H$^+$, 100%).
NMR δH (d$_6$-DMSO) 12.41 (1H, s), 7.41-7.11 (4H, m), 4.72 (1H, t), 4.39 (2H, m), 4.21 (1H, m), 3.47-3.29 (2H, m), 1.09 (3H, d).

EXAMPLE 6

5-[[(2,3-difluorophenyl)methyl]thio]-7-[[2-hydroxyethoxy)ethyl]amino]thiazolo[4,5-d]pyrimidin-2(3H)-one (a) 2-[2-[[2-amino-5-[[(2,3-difluorophenyl)methyl]thio]thiazolo[4,5-d]pyrimidin-7-yl]amino]ethoxy]ethanol Prepared by the method of example 2 step a), using the product of example 4, step b) and 2-(2-aminoethoxy)-ethanol.
MS (APCI) 414 (M+H$^+$, 100%).

(b) 2-[2-[[2-bromo-5-[[(2,3-difluorophenyl)methyl]thio]thiazolo[4,5-d]pyrimidin-7-yl]amino]ethoxy]ethanol Prepared by the method of example 1 step e), using the product of example 6 step a).
MS (APCI) 478 (M+H$^+$, 100%).

(c) 2-[2-[[5-[[(2,3-difluorophenyl)methyl]thio]-2-methoxythiazolo[4,5-d]pyrimidin-7-yl]amino]ethoxy]ethanol Prepared by the method of example 1 step f), using the product of example 6 step b).
MS (APCI) 429 (M+H$^+$, 100%).

(d) 5-[[(2,3-difluorophenyl)methyl]thio]-7-[[2-(2-hydroxyethoxy)ethyl]amino]thiazolo[4,5-d]pyrimidin-2(3H)-one Prepared by the method of example 1 step g), using the product of example 6 step c).
M.P 213-4° C.
MS (APCI) 415 (M+H$^+$, 100%).
NMR δH (d$_6$-DMSO) 12.41 (1H, s), 7.39-7.11 (4H, m), 4.57 (1H, t), 4.39 (2H, s), 3.57-3.38 (8H, m).

EXAMPLE 7

5-[[(2,3-difluorophenyl)methyl]thio]-7-[[2-hydroxy-1-(hydroxymethyl)ethyl]amino]thiazolo[4,5-d]pyrimidin-2(3H)-one (a) 2-[[2-amino-5-[[(2,3-difluorophenyl)methyl]thio]thiazolo[4,5-d]pyrimidin-7-yl]amino]-1,3-propanediol Prepared by the method of example 2 step a), using the product of example 4, step b) and 2-amino-1,3-propandiol.
MS (APCI) 400 (M+H$^+$, 100%).

(b) 2-[[2-Bromo-5-[[(2,3-difluorophenyl)methyl]thio]thiazolo[4,5-d]pyrimidin-7-yl]amino]-1,3-propanediol Prepared by the method of example 1 step e), using the product of example 7 step a).
MS (APCI) 464 (M+H$^+$, 100%).

(c) 2-[[5-[[(2,3-difluorophenyl)methyl]thio]-2-methoxythiazolo[4,5-d]pyrimidin-7-yl]amino]-1,3-propanediol Prepared by the method of example 1 step f), using the product of example 7 step b).
MS (APCI) 415 (M+H$^+$, 100%).

(d) 5-[[(2,3-difluorophenyl)methyl]thio]-7-[[2-hydroxy-1-(hydroxymethyl)ethyl]amino]thiazolo[4,5-d]pyrimidin-2(3H)-one Prepared by the method of example 1 step g), using the product of example 7 step c).
M.P 178-9° C.
MS (APCI) 401 (M+H$^+$, 100%).
NMR δH (d$_6$-DMSO) 12.41 (1H, s), 7.42-7.11 (4H, m), 4.66 (2H, s), 4.40 (2H, s), 4.19 (1H, m), 3.49 (4H, m).

EXAMPLE 8

7-[(2-aminoethyl)amino]-5-[[(2,3-difluorophenyl)methyl]thio]thiazolo[4,5-d]pyrimidin-2(3H)-one a) [2-[[2-amino-5-[[(2,3-difluorophenyl)methyl]thio]thiazolo[4,5-d]pyrimidin-7-yl]amino]ethyl]-carbamic acid, 1,1-dimethylethyl ester Prepared by the method of example 2 step a), using the product of example 4, step b) and (2-aminoethyl)-carbamic acid, 1,1-dimethylethyl ester.
MS (APCI) 469 (M+H$^+$, 100%).

b) [2-[[2-bromo-5-[[(2,3-difluorophenyl)methyl]thio]thiazolo[4,5-d]pyrimidin-7-yl]amino]ethyl]-carbamic acid, 1,1-dimethylethyl ester Prepared by the method of example 1 step e), using the product of example 8 step a).
MS (APCI) 533 (M+H$^+$, 100%).

c) [2-[[5-[[(2,3-difluorophenyl)methyl]thio]-2-methoxythiazolo[4,5-d]pyrimidin-7-yl]amino]ethyl]carbamic acid, 1,1-dimethylethyl ester Prepared by the method of example 1 step f), using the product of example 8 step b).
MS (APCI) 489 (M+H$^+$, 100%).

d) 7-[(2-aminoethyl)amino]-5-[[(2,3-difluorophenyl)methyl]thio]thiazolo[4,5-d]pyrimidin-2(3H)-one Prepared by the method of example 1 step g), using the product of example 8 step c).
M.P 215-6° C.
MS (APCI) 370 (M+H$^+$, 100%).
NMR δH (d$_6$-DMSO) 12.00 (1H, s), 7.45-7.11 (3H, m), 6.35 (1H, bs), 4.37 (2H, s), 3.48 (2H, m), 2.92 (2H, t),

EXAMPLE 9

5-[[(2,3-difluorophenyl)methyl]thio]-7-[(2-hydroxyethyl)amino]thiazolo[4,5-d]pyrimidin-2(3H)-one (a) 2-[[2-amino-5-[[(2, difluorophenyl)methyl]thio]thiazolo[4,5-d]pyrimidin-7-yl]amino]ethanol Prepared by the method of example 2 step a), using the product of example 4, step, b) and ethanolamine
MS (APCI) 370 (M+H$^+$, 100%).

(b) 2-[[2-bromo-5-[[(2,3-difluorophenyl)methyl]thio]thiazolo[4,5-d]pyrimidin-7-yl]amino]ethanol, Prepared by the method of example 1 step e), using the product of example 9 step a).
MS (APCI) 434 (M+H$^+$, 100%).

(c) 2-[[5-[[(2,3-difluorophenyl)methyl]thio]-2-methoxythiazolo[4,5-d]pyrimidin-7-yl]amino]ethanol Prepared by the method of example 1 step f), using the product of example 9 step b).
MS (APCI) 385 (M+H$^+$, 100%).

(d) 5-[[(2,3-difluorophenyl)methyl]thio]-7-[(2-hydroxyethyl)amino]thiazolo[4,5-d]pyrimidin-2(3H)-one Prepared by the method of example 1 step g), using the product of example 9 step c).
M.P 217-9° C.
MS (APCI) 371 (M+H$^+$, 100%).
NMR δH (d$_6$-DMSO) 12.43 (1H, s), 7.67-7.64 (1H, m), 7.39-7.33 (2H, m), 7.16-7.12 (1H, m), 4.73 (1H, t), 4.40 (2H, s), 3.52-3.42 (4H, m).

EXAMPLE 10

N-[2-[[5-[[(2,3-difluorophenyl)methyl]thio]-2,3-dihydro-2-oxothiazolo[4,5-d]pyrimidin-7-yl]amino]ethyl]methanesulfonamide a) N-[2-[[2-amino-5-[[(2,3-difluorophenyl)methyl]thio]thiazolo[4,5-d]pyrimidin-7-yl]amino]ethyl]methanesulfonamide Prepared by the method of example 2 step a), using the product of example 4, step b) and N-[2-aminoethyl]-methanesulfonamide,
MS (APCI) 448 (M+H$^+$, 100%).

b) N-[2-[[2-bromo-5-[[(2,3-difluorophenyl)methyl]thio]thiazolo[4,5-d]pyrimidin-7-yl]amino]ethyl]methanesulfonamide Prepared by the method of example 1 step e), using the product of example 10 step a).
MS (APCI) 511 (M+H$^+$; 100%).

c) N-[2-[[5-[[(2,3-difluorophenyl)methyl]thio]-2-methoxythiazolo[4,5-d]pyrimidin-7-yl]amino]ethyl]methanesulfonamide Prepared by the method of example 1 step f), using the product of example 10 step b).
MS (APCI) 462 (M+H$^+$, 100%).

d) N-[2-[[5-[[(2,3-difluorophenyl)methyl]thio]-2,3-dihydro-2-oxothiazolo[4,5-d]pyrimidin-7-yl]amino]ethyl]methanesulfonamide Prepared by the method of example 1 step g), using the product of example 10 step c).
M.P 225-6° C.
MS (APCI) 448 (M+H$^+$, 100%).
NMR δH (d$_6$-DMSO) 12.49 (1H, s), 7.72 (1H, t), 7.41-7.13 (4H, m), 4.43 (2H, bs), 3.49 (2H, m), 3.13 (2H, m), 2.89 (3H, s).

EXAMPLE 11

(+/−)-5-[[(2,3-difluorophenyl)methyl]thio]-7-[[2-(2-hydroxyethoxy)-1-methylethyl]amino]thiazolo[4,5-d]pyrimidin-2(3H)-one a) (+/−)-2-[2-[[2-amino-5-[[(2,3-difluorophenyl)methyl]thio]thiazolo[4,5-d]pyrimidin-7-yl]amino]propoxy]ethanol Prepared by the method of example 2 step a), using the product of example 4, step b) and (+/−)-2-[2-aminopropoxy]ethanol,
MS (APCI) 428 (M+H$^+$, 100%).

b) (+/−)-2-[2-[[2-bromo-5-[[(2,3-difluorophenyl)methyl]thio]thiazolo[4,5-d]pyrimidin-7-yl]amino]propoxy]ethanol Prepared by the method of example 1 step e), using the product of example 11 step a).
MS (APCI) 492 (M+H$^+$, 100%).

c) (+/−)-2-[2-[[5-[[(2,3-difluorophenyl)methyl]thio]-2-methoxythiazolo[4,5-d]pyrimidin-7-yl]amino]propoxy]ethanol Prepared by the method of example 1 step f), using the product of example 11 step b).
MS (APCI) 443 (M+H$^+$, 100%).

d) (+/−)-5-[[(2,3-difluorophenyl)methyl]thio]-7-[[2-(2-hydroxyethoxy)-1-methylethyl]amino]thiazolo[4,5-d]pyrimidin-2(3H)-one Prepared by the method of example 1 step g), using the product of example 11 step c).
M.P 221-2° C.
MS (APCI) 429 (M+H$^+$, 100%).
NMR δH (d$_6$-DMSO) 12.43 (1H, s), 7.47-7.30 (3H, m), 7.17-7.13 (1H, m), 4.56 (1H, t), 4.40 (2H, s), 4.35 (1H, m), 3.49-3.32 (6H, m), 1.10 (3H, d).

EXAMPLE 12

7-[[(1R)-2-amino-1-methylethyl]amino]-5-[[(2,3-difluorophenyl)methyl]thio]thiazolo[4,5-d]pyrimidin-2(3H)-one trifluoroacetate (a) (2R)-2-[[2-amino-5-[[(2,3-difluorophenyl)methyl]thio]thiazolo[4,5-d]pyrimidin-7-yl]amino]propanamide Prepared by the method of example 2 step a), using the product of example 4, step b) and (2R)-2-amino-propanamide hydrochloride,
MS (APCI) 397 (M+H$^+$, 100%).

(b) N'-[(1R)-2-amino-1-methylethyl]-5-[[(2,3-difluorophenyl)methyl]thio]thiazolo[4,5-d]pyrimidine-2,7-diamine To a solution of the product from example 12 step a) (0.3 g) in dry tetrahydrofuran (10 ml) was added 2M borane in THF (10 ml) and the mixture heated under reflux for 6 hours. Quenched while hot with methanol (30 ml), evaporated to dryness and the residue taken up into methanol (30 ml) containing a few drops of concentrated hydrochloric acid. The mixture was then heated under reflux for a further 1 hour, evaporated to dryness to give a pale yellow solid.
MS (APCI) 383 (M+H$^+$, 100%).

(c) [(2R)-2-[[2-amino-5-[[(2,3-difluorophenyl)methyl]thio]thiazolo[4,5-d]pyrimidin-7-yl]amino]propyl]carbamic acid, 1,1-dimethylethyl ester To a solution of the product from example 12 step b) (1.6 g) in THF (50 ml) was added di-tert-butyldicarbonate (0.91 g) and the mixture stirred for 2 days. Evaporated to dryness to give 2.0 g.
MS (APCI) 483 (M+H$^+$, 100%).

(d) [(2R)-2-[[2-bromo-5-[[(2,3-difluorophenyl)methyl]thio]thiazolo[4,5-d]pyrimidin-7-yl]amino]propyl]carbamic acid, 1,1-dimethylethyl ester Prepared by the method of example 1 step e), using the product of example 12 step c).
MS (APCI) 547 (M+H$^+$, 100%).

(e) [(2R)-2-[[5-[[(2,3-difluorophenyl)methyl]thio]-2-methoxythiazolo[4,5-d]pyrimidin-7-yl]amino]propyl]carbamic acid, 1,1-dimethylethyl ester Prepared by the method of example 1 step f), using the product of example 12 step d).
MS (APCI) 498 (M+H$^+$, 100%).

(f), 7-[[(1R)-2-amino-1-methylethyl]amino]-5-[[(2,3-difluorophenyl)methyl]thio]thiazolo[4,5-d]pyrimidin-2(3H)-one trifluoroacetate, Prepared by the method of example 1 step g), using the product of example 12 step e) and purified by the method of example 15 step f).
MS (APCI) 384 (M+H$^+$, 100%).
NMR δH (d$_6$-DMSO) 12.55 (1H, s), 7.81 (3H, bs), 7.45-7.31 (4H, m), 7.18-7.13 (1H, m), 4.51-4.34 (3H, m), 2.95 (2H, m), 1.14 (3H, d).

EXAMPLE 13

5-[[(2,3-difluorophenyl)methyl]thio]-7-[[(1R)-2-[(2-hydroxyethyl)amino]-1-methylethyl]amino]thiazolo[4,5-d]pyrimidin-2(3H)-one trifluoroacetate To a solution of the product from example 12 step f) (100 mg) in dry THF (5 ml) was added [[(1,1-dimethylethyl)dimethylsilyl]oxy]-acetaldehyde (49 mg) followed by sodium triacetoxyborohydride (61 mg) and the mixture stirred for 1 hour. The mixture was acidified with concentrated hydrochloric acid, stirred at room temp for 1 hour then evaporated to dryness. The product was purified (HPLC, Novapak® C18 column, 0.1% aqueous TFA:acetonitrile, gradient elution 75:25 to 5:95 over 15 minutes) to afford the title compound (0.021 g).
MS (APCI) 428 (M+H$^+$, 100%).
NMR δH (d$_6$-DMSO) 7.39-7.29 (2H, m), 7.17-12 (1H, m), 6.92 (1H, m), 4.91 (1H, s), 4.48-4.32 (3H, m), 3.54 (2H, m), 2.94-2.82 (4H, m), 1.12 (3H, m).

EXAMPLE 14

5-[[(2,3-difluorophenyl)methyl]thio]-7-[[(1R)-2-(dimethylamino)-1-methylethyl]amino]thiazolo[4,5-d]pyrimidin-2(3H)-one Prepared by the method of example 13 using the product of example 12, step f) and 40% aqueous formaldehyde solution.
MS (APCI) 412 (M+H$^+$, 100%).
NMR δH (d$_6$-DMSO) 12.00 (1H, s), 7.39-7.31 (2H, m), 7.18-7.09 (2H, m), 4.39 (2H, q), 4.30 (1H, m), 3.31 (6H, bs), 2.43-2.38 (1H, m), 2.24-20 (1H, m), 1.07 (3H, d).

EXAMPLE 15

5-[[[4-(2-aminoethoxy)-3-chlorophenyl]methyl]thio]-7-[[(1R)-2-hydroxy-1-methylethyl]amino]thiazolo[4,5-d]pyrimidin-2(3H)-one trifluoroacetate (a) 2-(2-chloro-4-formylphenoxy)acetamide To a solution of 3-chloro-4-hydroxybenzaldehyde (10 g) in methanol (100 ml) was added 1.0 M potassium t-butoxide (64 ml). To the mixture was added 2-chloroacetamide (5.96 g) and the mixture heated under reflux overnight. The mixture was evaporated to the residue triturated with water (500 ml) and the solid collected to give the subtitle compound (4.4 g).
NMR δH (CDCl$_3$) 9.89 (1H, s), 7.97 (1H, d), 7.82 (1H, dd), 7.04 (1H, d), 6.73 (1H, s), 5.87 (1H, s), 4.63 (2H, s).

(b) 2-[2-chloro-4-(hydroxymethyl)phenoxy]acetamide

To a solution of the product from example 15 step a) (4.4 g) in ethanol (500 ml) was added sodium borohydride (1.56 g) and the mixture allowed to stir for 1 hour. Acidified with glacial acetic acid, evaporated to dryness and extracted into ethyl acetate, washed with water to give the subtitle compound (4.3 g).
NMR δH (CDCl$_3$) 7.44 (1H, d), 7.29 (1H, d), 6.90 (1H, d), 6.81 (1H, s), 5.85 (1H, s), 4.63 (2H, s), 4.48 (2H, s), 1.96 (1H, s).

(c) 2-[4-[(acetylthio)methyl]-2-chlorophenoxy]acetamide

Diisopropylazocarboxylate (5.5 ml) was added to a stirred solution of triphenylphosphine (7.31 g) in THF at 0° C. Upon completion of addition a colourless precipitate deposited. To this suspension was added a mixture of the product from example 15 step b) (3.0 g) and thiolacetic acid (2.00 ml) in THF (30 ml) at 0° C. The mixture was allowed to attain room temp overnight, evaporated to dryness and the residue purified (SiO$_2$, 10% ethyl acetate: 90% ether as eluant) to give the subtitle compound (3.5 g).
NMR δH (CDCl$_3$) 7.35 (1H, d), 7.17 (1H, dd), 6.84 (1H, d), 6.76 (1H, s), 5.81 (1H, s), 4.54 (2H, s), 4.04 (2H, s), 2.35 (3H, s).

(d) 2-[2-chloro-4-(mercaptomethyl)phenoxy]acetamide

To a solution of the product from example 15 step c) (1.0 g) in methanol (50 ml) was added sodium hydroxide pellets (0.15 g) and the mixture stirred for 2 days. The mixture was diluted with water and the subtitle compound collected by filtration. (0.7 g).
NMR δH (d6 DMSO) 7.44 (1H, s), 7.38 (1H, d), 7.21 (1H, dd), 6.98 (1H, d), 4.55 (2H, s), 3.76 (2H, s).

(e) 7-[[(1R)-2-hydroxy-1-methylethyl]amino]-5-[(phenylmethyl)sulfonyl]thiazolo[4,5-d]pyrimidin-2(3H)-one To a solution of the product from example 3 step d)(240 mg) in acetonitrile (100 ml) and water (100 ml) was added oxone (2.4 g) and the mixture heated at 40 deg for 2 hours. The acetonitrile was removed by rotary evaporation and the subtitle compound collected by filtration (235 mg)
MS (APCI) 381 (M+H$^+$, 100%).

(f) 5-[[[4-(2-aminoethoxy)-3-chlorophenyl]methyl]thio]-7-[[(1R)-2-hydroxy-1-methylethyl]amino]thiazolo[4,5-d]pyrimidin-2(3H)-one trifluoroacetate To a mixture of the product from example 15 step e) (100 mg), the product from example 15 step d) (329 mg) and sodium borohydride (50 mg) in a solution of DMSO (1 ml) and ethanol (10 ml) was heated at 55-60° C. for 12 hours. The reaction mixture was evaporated to dryness and the residue purified (HPLC, Novapak® C18 column, 0.1% aqueous TFA: acetonitrile, gradient elution 95:5 to 5:95 over 15 minutes) to afford the title compound (0.02-3 g).
MS (APCI) 442 (M+H$^+$, 100%).
NMR δH (D$_2$O) 7.46 (1H, bs), 7.32 (1H, d), 7.00 (1H, d), 4.36-4.20 (5H, m), 3.61 (2H, m), 3.46 (2H, m), 1.20 (3H, d).

EXAMPLE 16

5-[[3-Chloro-4-methoxyphenyl)methyl]thio]-7-[[(1R)-2-hydroxy-1-methylethyl]amino]thiazolo[4,5-d]pyrimidin-2(3H)-one a) 3-chloro-4-methoxybenzenemethanethiol Thiourea (3.04 g, 0.04 mol) was added to a solution of 3-chloro-4-methoxybenzyl bromide (4.0 g, 0.02 mol) in ethanol (200 ml) and refluxed for 16 hours. The reaction mixture was concentrated in vacuo and the residue was subsequently dissolved in aqueous sodium hydroxide solution (30 g, 0.75 mol in 300 ml water) and heated at 80° C. for one hour. The reaction mixture was cooled with an ice bath and acidified by addition of concentrated hydrochloric acid. The product was isolated by extraction three times into diethyl ether. The combined organic phases were dried over anhydrous magnesium sulfate, filtered and concentrated in vacuo, to give the subtitle compound as a colourless oil in 83% yield (3.0 g).
NMR δH (CDCl$_3$) 7.34 (1H, m), 7.18 (1H, dd), 6.86 (1H, d), 3.89 (3H, s), 3.68 (2H, d), 1.76 (1H, t).

b) 5-[[3-Chloro-4-methoxyphenyl)methyl]thio]-7-[[(1R)-2-hydroxy-1-methylethyl]amino]thiazolo[4,5-d]pyrimidin-2(3H)-one 3-chloro-4-methoxybenzenemethanethiol (0.128 g, 0.68 mmol), prepared in example 16 step a), the product of example 15 step e) (0.130 g, 0.349 mmol), and sodium borohydride (0.026 g, 0.68 mmol) were refluxed at 50° C. in a mixture of dimethylsulfoxide (6 ml) and ethanol (10 ml). After 3 hours and again after five hours reaction time, further portions of sodium borohydride (0.05 g, 1.3 mmol) in ethanol (2 ml) were added to the reaction and reflux at 50° C. was continued until conversion was complete by hplc ms (15 hours in total). The reaction mixture was neutralised by addition of concentrated hydrochloric acid and the ethanol removed in vacuo. The residue was purified by reverse phase chromatography on Symmetry C8, eluting with a gradient of 25% to 95% acetonitrile in 0.1M aqueous ammonium acetate over 10 minutes. The product was freeze dried from methanol/water/acetonitrile to obtain the sub-title compound in 33% yield as a white lyophylate (0.046 g).
MS (APCI) 413 (M+H$^+$, 100%).
NMR δH (d$_6$-DMSO) 12.39 (1H, bs), 7.47 (1H, m), 7.36 (1H, m), 7.25 (1H, d), 7.06 (1H, d), 4.72 (1H, t), 4.32-4.21 (3H, m), 3.82 (3H, s), 3.49-3.30 (2H, m), 1.11 (3H, d).

EXAMPLE 17

5-[[3-Chloro-2-fluorophenyl)methyl]thio]-7-[[(1R-2-hydroxy-1-methylethyl]amino]thiazolo[4,5-d]pyrimidin-2(3H)-one a) 3-chloro-2-fluorobenzenemethanethiol The subtitle compound was prepared as a colourless oil in 65% yield (2.51 g) by the method described in example 16 step a) from 3-chloro-2-fluorobenzyl bromide (5.0 g, 0.022 mol).
NMR δH (CDCl$_3$) 7.32-7.21 (2H, m), 7.04 (1H, t), 3.75 (2H, d), 1.90 (1H, t).

b) 5-[[3-Chloro-2-fluorophenyl)methyl]thio]-7-[[(1R)-2-hydroxy-1-methylethyl]amino]thiazolo[4,5-d]pyrimidin-2(3H)-one The title compound was prepared by the method described in example 16 step b) from 3-chloro-2-fluorobenzenemethanethiol, prepared in example 17 step a), and the product of example 15 step e).
The product was obtained in 12% yield as a white lyophylate (0.038 g).
M.P 234-5° C.
MS (APCI) 401 (M+H$^+$, 100%).
NMR δH (d$_6$-DMSO) 12.4 (1H, bs), 7.55 (1H, m), 7.48 (1H, t), 7.26 (1-H, d), 7:17 (1H, t), 4.72 (1H, bs), 4.38 (2H, m), 4.19 (1H, m), 3.3 (2H, m), 1.08 (3H, d).

EXAMPLE 18

5-[[(2,3-Difluorophenyl)methyl]thio]-7-[[(3R,4R)-4-hydroxypyrrolidin-3-yl]amino]-thiazolo[4,5-d]pyrimidin-2(3H)-one (a) 3-[[2-amino-5-[[(2,3-difluorophenyl)methyl]thio]thiazolo[4,5-d]pyrimidin-7-yl]amino]-4-hydroxy-(3R,4R)-1-pyrrolidinecarboxylic acid, 1,1-dimethylethyl ester (3R,4R)-3-Amino-4-hydroxy-1-pyrrolidinecarboxylic acid, 1,1-dimethylethyl ester (0.73 g), diisopropylethylamine (1.0 ml) and the product of example 4 step b), were stirred in NMP (10 ml) at 100° C. for 28 hrs. The cooled mixture was poured onto water and the solid produced collected, washed with water and air dried. The crude material was purified (SiO$_2$, ethyl acetate as eluant) to give the subtitle compound as a colourless solid (0.58 g).
m.p. 182-5° C.
MS (APCI) 511 (M+H, 100%).

(b) 3-[[2-Bromo-5-[[(2,3-difluorophenyl)methyl]thio]thiazolo[4,5-d]pyrimidin-7-yl]amino]-4-hydroxy-(3R,4R)-1-pyrrolidinecarboxylic acid, 1,1-dimethylethyl ester Prepared by the method of example 1 step e), using the product of example 18 step a).
MS (APCI) 572 (M−H$^+$, 100%).

(c) 3-[[5-[[(2,3-Difluorophenyl)methyl]thio]-2-methoxythiazolo[4,5-d]pyrimidin-7-yl]amino]-4-hydroxy-(3R,4R)-1-pyrrolidinecarboxylic acid, 1,1-dimethylethyl ester Prepared by the method of example 1 step f), using the product of example 18 step b).
MS (APCI) 526 (M+H$^+$, 100%).

(d) 5-[[(2,3-Difluorophenyl)methyl]thio]-7-[[(3R,4R)-4-hydroxypyrrolidin-3-yl]amino]thiazolo[4,5-d]pyrimidin-2(3H)-one Prepared by the method of example 1 step g), using the product of example 18 step c).
m.p. 270° C. dec)
MS (APCI) 412 (M+H$^+$, 100%).
NMR δH (d$_6$-DMSO) 7.32 (2H, m), 7.14 (1H, m), 6.46 (1H, d), 5.57 (1H, s), 4.39 (2H, s), 4.30 (2H, m), 3.39 (2H, m), 3.12 (1H, dd), 2.98 (1H, d).

EXAMPLE 19

5-[[(2,3-Difluoroiphenyl)methyl]thio]-7-[(3R)-pyrrolidin-3-ylamino]thiazolo[4,5-d]pyrimidin-2(3H)-one dihydrochloride (a) 3-[[2-Amino-5-[[(2,3-difluorophenyl)methyl]thio]thiazolo[4,5-d]pyrimidin-7-yl]amino]-(3R)-1-pyrrolidinecarboxylic acid, 1,1-dimethylethyl ester Prepared by the method of example 18 step a) using (R)-3-amino-1-pyrrolidinecarboxylic acid, 1,1-dimethylethyl ester and the product of example 4 step b).
MS (APCI) 495 (M+H$^+$, 100%).

(b) 3-[[2-Bromo-5-[[(2,3-difluorophenyl)methyl]thio]thiazolo[4,5-d]pyrimidin-7-yl]amino]-(3R)-1-pyrrolidinecarboxylic acid, 1,1-dimethylethyl ester Prepared by the method of example 1 step e), using the product of example 19 step a).
MS (APCI) 559 (M+H$^+$, 100%).

(c) 3-[[5-[[(2,3-Difluorophenyl)methyl]thio]-2-methoxythiazolo[4,5-d]pyrimidin-7-yl]amino]-(3R)-1-pyrrolidinecarboxylic acid, 1,1-dimethylethyl ester Prepared by the method of example 1 step f), using the product of example 19 step b).
MS (APCI) 510 (M+H$^+$, 100%).

(d) 5-[[(2,3-Difluorophenyl)methyl]thio]-7-[(3R)-pyrrolidin-3-ylamino]thiazolo[4,5-d]pyrimidin-2(3H)-one, dihydrochloride Prepared by the method of example 1 step g), using the product of example 19 step c) then converted to the salt.
m.p. 178-181° C.
MS (APCI) 396 (M+H$^+$, 100%).
NMR δH (d$_6$-DMSO) 12.75 (1H, s), 9.19 (2H, bd); 7.91 (1H, d), 7.37 (2H, m), 7.17 (1H, m), 4.66 (1H, m), 4.43 (2H, dd), 3.10-3.50 (4H, m), 2.17 (1H, m), 1.96 (1H, m).

EXAMPLE 20

7-[[(1R)-2-Hydroxy-1-methylethyl]amino]-5-[[(2-methyl-4-thiazolyl)methyl]thio]thiazolo[4,5-d]pyrimidin-2(3H)-one (a) 6-Amino-2-[[(2-methyl-4-thiazolyl)methyl]thio]-4(3H)-pyrimidinone 4-Amino-6-hydroxy-2-mercaptopyrimidine hydrate (16.1 g) and powdered sodium hydroxide, (8.0 g) was stirred in dry DMF (100 ml) for 20 mins. 4-Chloromethyl-2-methylthiazole hydrochloride monohydrate (20 g) was added portionwise and the resulting suspension stirred 18 hrs. The mixture was poured onto water and the solid collected, washed with water and dried to afford the sub-title compound (24.3 g)
MS (APCI) 255 (M+H$^+$, 100%).

(b) 2-Amino-5-[[(2-methyl-4-thiazolyl)methyl]thio]thiazolo[4,5-d]pyrimidin-7(6H)-one The product from example 20 step a) (24.3 g) and potassium thiocyanate (37.1 g) was stirred in dry DMF (400 ml) with pyridine (13.1 ml) at 0° C. Bromine (4.5 ml) was added over 1 hr. After stirring 2 hrs the mixture was poured into water. The resulting solution was concentrated to low volume then water added. The resulting solid was collected, taken up in 2M hydrochloric acid and precipitated by the addition of saturated sodium bicarbonate solution. The solid was collected, washed with water and dried to give the sub-title compound, (8.7 g).
MS (APCI) 312 (M+H$^+$, 100%).

(c) 7-Chloro-5-[[(2-methyl-4-thiazolyl)methyl]thio]thiazolo[4,5-d]pyrimidin-2-amine Prepared by the method of example 1 step c), using the product of example 20 step b), (4.3 g).
MS (APCI) 330/332 (M+H$^+$), 330 (100%).

(d) (2R)-2-[[2-Amino-5-[[(2-methyl-4-thiazolyl)methyl]thio]thiazolo[4,5-d]pyrimidin-7-yl]amino]-1-propanol Prepared by the method of example 18 step a), using the product of example 20 step c),
m.p. 220-2° C.
MS-(APCI) 369 (M+H, 100%).

(e) (2R)-2-[[2-Bromo-5-[[(2-methyl-4-thiazolyl)methyl]thio]thiazolo[4,5-d]pyrimidin-7-yl]amino]-1-propanol Prepared by the method of example 1 step e), using the product of example 20 step d).
MS (APCI) 433 (M+H$^+$, 100%).

(f) (2R)-2-[[2-Methoxy-5-[[(2-methyl-4-thiazolyl)
methyl]thio]thiazolo[4,5-d]pyrimidin-7-yl]amino]-1-
propanol Prepared by the method of example 1 step f), using the product of example 20 step e).
MS (APCI) 384 (M+H$^+$, 100%).

(g) 7-[[(1R)-2-Hydroxy-1-methylethyl]amino]-5-
[[(2-methyl-4-thiazolyl)methyl]thio]thiazolo[4,5-d]
pyrimidin-2(3H)-one Prepared by the method of example 1 step g), using the product of example 20 step f).
m.p. 208-9° C.
MS (APCI) 370 (M+H$^+$, 100%).
NMR δH (d$_6$-DMSO) 12.37 (1H, s), 7.35 (1H, s), 7.32 (1H, d), 4.73 (1H, t), 4.36 (2H, s), 4.21 (1H, m), 3.38 (2H, m), 2.62 (3H, s), 1.10 (3H, d).

EXAMPLE 21

7-[[2-Hydroxy-1-(hydroxymethyl)ethyl]amino]-5-
[[(2-methyl-4-thiazolyl)methyl]thio]thiazolo[4,5-d]
pyrimidin-2(3H)-one (a) 2-[[2-amino-5-[[(2-methyl-4-thiazolyl)methyl]
thio]thiazolo[4,5-d]pyrimidin-7-yl]amino]-1,3-pro-
panediol Prepared by the method of example 18 step a), using the product of example 20 step c) and 2-amino-1,3-propanediol
m.p. 158-160° C.
MS (APCI) 385 (M+H, 100%).

(b) 2-[[2-Bromo-5-[[(2-methyl-4-thiazolyl)methyl]
thio]thiazolo[4,5-d]pyrimidin-7-yl]amino]-1,3-pro-
panediol Prepared by the method of example 1 step e), using the product of example 21 step a).
MS (APCI) 448 (M+H$^+$, 100%).

(c) 2-[[2-Methoxy-5-[[(2-methyl-4-thiazolyl)methyl]
thio]thiazolo[4,5-d]pyrimidin-7-yl]amino]-1,3-pro-
panediol Prepared by the method of example 1 step f), using the product of example 21 step b).
MS (APCI) 400 (M+H$^+$, 100%).

(d) 7-[[2-Hydroxy-1-(hydroxymethyl)ethyl]amino]-
5-[[(2-methyl-4-thiazolyl)methyl]thio]thiazolo[4,5-
d]pyrimidin-2(3H)-one Prepared by the method of example 1 step g), using the product of example 21 step c).
m.p. 239-243° C.
MS (APCI) 386 (M+H$^+$, 100%).

NMR δH (d$_6$-DMSO) 12.37 (1H, s), 7.38 (1H, s), 7.24 (1H, d), 4.67 (2H, t), 4.36 (2H, s), 4.20 (1H, m), 3.50 (4H, m), 2.62 (3H, s).

EXAMPLE 22

7-[(2-Hydroxy-1,1-dimethylethyl)amino]-5-[[(2-
methyl-4-thiazolyl)methyl]thio]thiazolo[4,5-d]pyri-
midin-2(3H)-one (a) 2-[[2-Amino-5-[[(2-methyl-4-thiazolyl)methyl]
thio]thiazolo[4,5-d]pyrimidin-7-yl]amino]-2-methyl-
1-propanol Prepared by the method of example 18 step a), using the product of example 20 step c) and 2-amino-2-methylpropanol
m.p. 250-252° C.
MS (APCI) 383 (M+H, 100%).

(b) 2-[[2-Bromo-5-[[(2-methyl-4-thiazolyl)methyl]
thio]thiazolo[4,5-d]pyrimidin-7-yl]amino]-2-methyl-
1-propanol Prepared by the method of example 1 step e), using the product of example 22 step a).
MS (APCI) 446 (M+H$^+$, 100%).

(c) 2-[[2-Methoxy-5-[[(2-methyl-4-thiazolyl)methyl]
thio]thiazolo[4,5-d]pyrimidin-7-yl]amino]-2-methyl-
1-propanol Prepared b) the method of example 1 step f), using the product of example 22 step b).
MS (APCI) 398 (M+H$^+$, 100%).

(d) 7-[(2-Hydroxy-1,1-dimethylethyl)amino]-5-[[(2-
methyl-4-thiazolyl)methyl]thio]thiazolo[4,5-d]pyri-
midin-2(3H)-one Prepared by the method of example 1 step g), using the product of example 22 step c).
m.p. 231-2° C.
MS (APCI) 384 (M+H$^+$, 100%).
NMR δH (d$_6$-DMSO) 12.36 (1H, s), 7.37 (1H, s), 6.61 (1H, bs), 4.80 (1H, t), 4.37 (2H, s), 3.55 (2H, d), 2.62 (3H, s), 1.31 (6H, s).

EXAMPLE 23

7-[(2-Hydroxy-1,1-dimethylethyl)amino]-5-[[(2-
methylphenyl)methyl]thio]thiazolo[4,5-d]pyrimidin-
2(3H)-one (a) 7-[(7-Hydroxy-1,1-dimethylethyl)amino]-5-
[(phenylmethyl)sulphonyl]thiazolo[4,5-d]pyrimidin-
2(3H)-one A stirred solution of the product from example 1 step g) (0.14 g) in glacial acetic acid (30 ml) was treated with peracetic acid (36/40% in acetic acid, 2 ml), stirred for 2 h, then at 50° C. for 1 h. The solution was quenched with an excess of dimethyl sulphide and evaporated to give a gum.
MS (APCI) 395 (M+H$^+$, 100%).

(b) 7-[(2-Hydroxy-1,1-dimethylethyl)amino]-5-[[(2-
methylphenyl)methyl]thio]thiazolo[4,5-d]pyrimidin-
2(3H)-one The product from example 23 step (a) was taken up in DMSO (1.73 ml), treated with potassium butoxide and divided into 3 portions. One portion was treated with 2-methylphenylmethyl mercaptan (0.053 g), stirred at 50° C. for 1 h for 2 h, neutralised with glacial acetic acid and subjected to preparative reverse phase HPLC on a 19×50 mm symmetry C8 column using 10 to 60% acetonitrile in 0.1% aqueous ammonium acetate over 6 nm in at 20 ml/min to give the titled compound.

MS (APCI) 377 (M+H$^+$, 100%).

NMR δH (d$_6$-DMSO) 1.33 (s, 6H); 2.35 (s, 3H); 3.57 (d, 2H); 4.33 (s, 2H); 4.82 (t, 1H); 6.57 (broad s, 1H); 7.12-7.20 (mult., 3H); 7.41 (d, 1H); 12.37 (broad s, 1H)

EXAMPLE 24

5-[(2-Furanylmethyl)thio]-7-[[(1R)-2-hydroxy-1-methylethyl]amino]thiazolo[4,5-d]pyrimidin-2(3H)-one (a) 7-[[(1R)-2-Hydroxy-1-methylethyl]amino]-5-[(phenylmethyl)sulphonyl]thiazolo[4,5-d]pyrimidin-2(3H)-one The subtitled compound was prepared from the product of example 3 step d), using the method of example 23, step (a)
MS (ES) 381 (M+H$^+$, 100%).

(b) 5-[(2-Furanylmethyl)thio]-7-[[(1R)-2-hydroxy-1-methylethyl]amino]thiazolo[4,5-d]pyrimidin-2(3H)-one The titled compound was prepared from the product of example 24 step (a), using the method of example 23, step (b) using furfuryl mercaptan
MS (APCI) 339 (M+H$^+$, 100%).
NMR δH (d$_4$-methanol) 1.12 (d, 3H); 3.41-3.45 (mult., 1H); 3.49-3.53 (mult., 1H); 4.24-4.32 (mult., 3H); 6.18-6.22 (mult., 2H); 7.29 (broad s, 1H).

EXAMPLE 25

7-[[(1R)-2-Amino-1-methylethyl]amino]-5-[[(3-chloro-2-fluorophenyl)methyl]thio]thiazolo[4,5-d]pyrimidin-2(3H)-one (a) [(1R)-2-amino-1-methyl-2-oxoethyl]carbamic acid, 9H-fluoren-9-ylmethyl ester A solution of D-Alaninamide hydrochloride (3 g) in 10% sodium carbonate solution (50 ml) and dioxan (50 ml) was treated with FMOC chloride (6.24 g) in dioxane (40 ml) and allowed to stir overnight. The mixture was diluted with water (500 ml) and the product collected by filtration and dried in vacuo to give 9.0 g of the subtitle compound.
MS (ESI) BP 311 (+H)

(b) [(1R)-2-amino-1-methylethyl]carbamic acid, 9H-fluoren-9-ylmethyl ester

To a solution of the product from example 25 step a) (6.9 g) in THF (100 ml) was added borane-methylsulfide complex (4.4 ml) and the mixture heated under reflux for 2 hours. The mixture was carefully quenched by the addition of methanol (100 ml), evaporated to dryness and the residue taken up into methanol (100 ml) and acidified to pH 1-2 with concentrated hydrochloric acid. Heated under reflux for 30 mins then evaporated to dryness. The residue was triturated with ether to give a solid, which was collected by filtration, dissolved in water and the free base precipitated by the addition of aqueous sodium bicarbonate solution to give the subtitle compound (3.1 g).
MS (ESI) BP 297 (+H)

(c) (2R)[2-(9H-Fluoren-9-ylmethoxycarbonylamino) propyl]carbamic acid, 1,1-dimethylethylester To a stirred solution of the product from example 25 step b) (3.0 g) in THF (100 ml) was added ditert-butyldicarbonate (2.2 g) and the mixture stirred at room temp for 30 mins. The mixture was evaporated to dryness and the crude product purified (SiO$_2$ dichloromethane as eluant) to give the subtitle compound (3.8 g).
NMR δH(CDCl$_3$) 7.76 (2H, m), 7.42 (2H, m), 7.39-26 (4H, s), 5.01 (1H, s), 4.85 (1H, s), 4.38 (2H, d), 4.19 (1H, t), 3.77 (1H, m), 3.18 (2H, m), 1.27 (9H, s).

(d) [(2R)-2-aminopropyl]carbamic acid, 1,1-dimethylethyl ester

To a solution of the product from example 25 step c) (3.8 g) in THF (100 ml) was added piperidine (5 ml) and the mixture allowed to stand for 1 hour at room temp. The mixture was evaporated to dryness and the residue purified (SiO$_2$, 5% methanol:dichloromethane as eluant) to give the subtitle compound as a colourless oil (1.7 g).
NMR δH (CDCl$_3$) 4.95 (1H, s), 3.13 (1H, m), 2.99 (1H, m), 2.87 (1H, m), 1.38 (9H, s), 1.08 (3H, d).

(e) [(2R)-2-[[2-amino-5-[(phenylmethyl)thio]thiazolo[4,5-d]pyrimidin-7-yl]amino]propyl]carbamic acid, 1,1-dimethylethyl ester The product from example 1 step c) (2.0 g) and the product from example 25 step d) (1.3 g) in a solvent of NMP (10 ml) containing Hunigs base (3 ml) was heated at 110° C. for 10 hours. The mixture was evaporated to dryness and purified (SiO$_2$, (1:1) dichloromethane:ethyl acetate as eluant) to give the subtitle compound (1.9 g).
MS (ESI) BP 447 (+H)

(f) [(2R)-2-[[2-amino-5-[(phenylmethyl)sulfonyl] thiazolo[4,5-d]pyrimidin-7-yl]amino]propyl]carbamic acid, 1,1-dimethylethyl ester To a solution of OXONE (7.0 g) in water (400 ml) was added sodium hydrogen carbonate until the pH was adjusted to 7.4. To this solution was added a solution of the product from example 25 step e), (1.9 g) in acetonitrile (100 ml) and the mixture heated at 40° C. for 2 hours. Upon completion of the reaction the acetonitrile was removed by rotary evaporation to give the subtitle compound (1.7 g).
MS (ESI) BP 479 (+H)

(g) 3-chloro-2-fluoro-benzenemethanethiol

A mixture of 3-chloro-2-fluorobenzylbromide (5.0 g), thiourea (3.4 g) in a solvent of ethanol (200 ml) was heated under reflux for 16 hours. The mixture was evaporated to dryness and to the residue was added a solution of sodium hydroxide (30 g) in water (300 ml) and the mixture heated under reflux for 1 hour. Allowed to cool to room temperature and acidified with concentrated hydrochloric acid, the product was extracted into ether to give the subtitle compound as an oil (2.51 g).
NMR δH (CDCl$_3$) 7.32-21 (2H, m), 7.04 (1H, t), 3.75 (2H, d), 1.90 (1H, t).

(h) [(2R)-2-[[2-amino-5-[[(3-chloro-2-fluorophenyl) methyl]thio]thiazolo[4,5-d]pyrimidin-7-yl]amino] propyl]carbamic acid, 1,1-dimethylethyl ester To a mixture of the product from example 25 step f) (1.2 g), the product from example 25 step g) (1.6 g) in a mixed solvent of ethanol (30 ml) and DMSO (5 ml) was added sodium borohydride (100 mg) and the mixture heated at 50° C. for 2 hours. The ethanol was removed by rotary evaporation and the crude product extracted into ethyl acetate and washed with water. The subtitle compound was obtained by purification ($SiO_2$, 1:1)dichloromethane:ethyl acetate as eluant) to give (1.95 g).
MS (ESI) BP 499 (+H)

(i) [(2R)-2-[[2-bromo-5-[[(3-chloro-2-fluorophenyl) methyl]thio]thiazolo[4,5-d]pyrimidin-7-yl]amino] propyl]carbamic acid, 1,1-dimethylethyl ester Prepared by the method of example 1 step e), using the product of example 25 step h).
MS (APCI) 562, ($M+H^+$, 100%).

(j) [(2R)-2-[[5-[[(3-chloro-2-fluorophenyl)methyl] thio]-2-methoxythiazolo[4,5-d]pyrimidin-7-yl] amino]propyl]carbamic acid, 1,1-dimethylethyl ester Prepared by the method of example 1 step f), using the product of example 25 step i).
MS (APCI) 514 ($M+H^+$, 100%).

(k) 7-[[(1R)-2-Amino-1-methylethyl]amino]-5-[[(3-chloro-2-fluorophenyl)methyl]thio]-thiazolo[4,5-d] pyrimidin-2-(3H)-one Prepared by the method of example 1 step g), using the product of example 25 step j).
M.P 241-3° C.
MS (APCI) 400 ($M+H^+$, 100%).
NMR δH ($d_6$-DMSO) 7.56 (1H, m), 7.49 (1H, m), 7.17 (1H, m), 7.05 (1H, bs), 4.44 (1H, m), 4.39 (2H, ab), 2.92 (2H, d), 1.13 (3H, d).

EXAMPLE 26

(2S)-2-[[5-[[(2,3-Difluorophenyl)methyl]thio]-2,3-dihydro-2-oxothiazolo[4,5-d]pyrimidin-7-yl]amino]-3-hydroxy-propanamide (a) (2S)-2-[[2-amino-5-[[(2,3-difluorophenyl)methyl]thio]thiazolo[4,5-d]pyrimidin-7-yl]amino]-3-hydroxy-propanamide The subtitled compound was prepared according to example 2 step (a) using the product of example 4 step b) (2 g, 6 mmol), 1-serinamide (0.66 g, 6 mmol), NMP (80 ml), and diisopropylethylamine (2 ml) to give the subtitled compound (1.36 g)
Mp 145-151° C.
MS (APCI) 413 ($M+H^+$, 100%).
NMR δH ($d_6$-DMSO) 8.10 (2H, brs), 7.40-7.07 (6H, m), 4.57 (1H, q), 4.43 (1H, d), 4.36 (1H, d), 3.71 (2H, d).

(b) (2S)-2-[[5-[[(2,3-Difluorophenyl)methyl]thio]-2, 3-dihydro-2-oxothiazolo[4,5-d]pyrimidin-7-yl] amino]-3-hydroxy-propanamide Prepared by consecutive-use of the methods of example 1 steps e), f), and g), using the product of example 26 step (a). The compounds formed during the separate steps were not purified or characterised.
MS (APCI) 414 ($M+H^+$, 100%).
NMR δH ($d_6$-DMSO) 12.47 (1H, br), 7.47 (1H, br), 7.42 (1H, s), 7.34 (2H, m), 7.13 (1H, m), 7.09 (1H, s), 4.90 (1H, t), 4.58 (1H, m) 4.39 (2H, m), 3.70 (2H, m).

EXAMPLE 27

7-[[(1R)-2-hydroxy-1-methylethyl]amino]-5-[(2-thienylmethyl)thio]thiazolo[4,5-d]pyrimidin-2(3H)-one a) 7-[[(1R)-2-hydroxy-1-methylethyl]amino]-5-[(2-thienylmethyl)thio]thiazolo[4,5-d]pyrimidin-2(3H)-one The title compound was prepared by the method described in example 16 step b) from the product of example 15 step e) (0.300 g, 0.79 mmol) and 2-thiophenemethanethiol (0.32 ml, 3.9 mmol).
The product was obtained in low 3% yield as a white lyophylate (0.010 g).
MS (APCI) 355 ($M+H^+$, 100%).
NMR $δ_H$ ($d_6$-DMSO) 12.50 (1H, bs), 7.36 (1H, m), 7.16 (1H, bs), 7.07 (1H, m), 6.92 (1H, m), 4.72 (1H, bs), 4.55 (2H, d), 4.26 (1H, m), 3.44 (2H, m), 1.12 (3H, d).

EXAMPLE 28

7-[[(1R)-2-hydroxy-1-methylethyl]amino]-5[[[3-methyl-4-(methylsulfonyl)phenyl]methyl]thio]thia-zolo[4,5-d]pyrimidin-2(3H)-one a) 3-methyl-4-(methylthio)benzaldehyde Tin (IV) chloride (13.6 ml, 0.116 mol) was added to an ice-bath cooled solution of 1-methyl-2-(methylthio)benzene (10 g, 0.073 mol) in anhydrous dichloromethane (200 ml) under nitrogen and stirred for a further 2 hours at 0° C. α,α-Dichloromethyl methyl ether (6.56 ml, 0.073 mol) was introduced and the reaction stirred for 1 hour at <10° C. before the cooling was removed. After attaining room temperature, the reaction mixture was poured into ice/water (400 ml), stirred and then extracted with dichloromethane (×3). The combined organic layers were dried over anhydrous magnesium sulfate, filtered, concentrated onto silica gel and purified by flash chromatography, eluting with diethyl ether/ isohexane (10:1) to yield the subtitle compound as a brown oil (6.54 g) in 54% yield.
GCMS 166 ($M^+$, 100%).
NMR $δ_H$ ($CDCl_3$) 9.91 (1H, s), 7.68 (1H, m), 7.62 (1H, s), 7.24 (1H, t), 2.54 (3H, s), 2.36 (3H, s).

b) 3-methyl-4-(methylthio)benzenemethanol

Sodium borohydride (1.40 g, 0.037 mol) was added to an ice-bath cooled solution of the product of example 28 step a) (6.16 g, 0.037 mol) in ethanol (50 ml). After 1 hour, the reaction mixture was neutralised by careful addition of aqueous hydrochloric acid (2 molar) and concentrated in vacuo to remove the organic solvent. The remaining aqueous solution was then extracted with ethyl acetate (×3). The combined organic layers were dried over anhydrous magnesium sulfate, filtered, and concentrated in vacuo to yield the subtitle compound as a brown oil (6 g) in quantitative yield.

GCMS 168 (M+, 100%).

NMR $\delta_H$ (CDCl$_3$) 7.18 (3H, m), 4.62 (2H, bs), 2.46 (3H, s), 2.33 (3H, s).

c) 3-methyl-4-(methylsulfonyl)benzenemethanol 3-chloroperoxybenzoic acid (57-86% grade, 20.4 g) was stirred in dichloromethane (150 ml), dried over anhydrous magnesium sulfate and then filtered. The filtrate was added dropwise over 1 hour to an ice-bath cooled, stirred solution of the product from example 28 step b) (5.67 g, 0.034 mol) in dichloromethane (50 ml). The reaction mixture was filtered and the filtrate washed with aqueous sodium hydrogen carbonate solution followed by aqueous sodium dithionite solution (10 g Na$_2$O$_4$S$_2$ in 150 ml water). The organic layer was dried over anhydrous magnesium sulfate, filtered, and concentrated in vacuo before purification by flash chromatography, eluting with dichloromethane/methanol (100:2). The sub-title compound was obtained as a yellow oil (5.52 g) in 82% yield.

MS (APCI) 201.1 (M+H+, 94.3%).

NMR $\delta_H$ (CDCl$_3$) 7.87 (1H, d), 7.38 (2H, m), 5.40 (1H, q), 4.56 (2H, d), 3.18 (3H, s), 2.61 (3H, s).

d) 3-methyl-4-(methylsulfonyl)benzenemethanethiol acetate

Diethyl azodicarboxylate (4.33 ml, 0.028 mol) was added to an ice-bath cooled solution of triphenylphosphine (7.20 g, 0.028 mol) in tetrahydrofuran (40 ml). To the resulting suspension was added a solution of the product from example 28 step c) (5.5 g, 0.028 mol) dissolved in tetrahydrofuran (20 ml). After the precipitate had dissolved, thiolacetic acid was added to the reaction solution and the cooling was removed. After 16 hours at room temperature, the reaction was concentrated onto silica gel and purified by flash chromatography, eluting with isohexane/ethyl acetate (2:1). The sub-title compound was obtained as a pink solid (2.46 g) in 35% yield.

NMR $\delta$H (d$_6$-DMSO) 7.84 (1H, d), 7.36 (2H, m), 4.16 (2H, s), 3.19 (3H, s), 2.61 (3H, s), 2.37 (3H, s).

e) bis[[3-methyl-4-(methylsulfonyl)phenyl]methyl] disulfide

A mixture of the product of example 28 step d) (1.98 g, 7.66 mmol) and 7 molar methanolic/ammonia (30 ml) was stirred for 24 hours. The product precipitated out of solution as a white solid and was isolated by filtration and dried in vacuo. The filtrate was similarly treated with 7 molar ammonia in methanol and yielded a second crop of solid, white product. In total, the sub-title compound was obtained in 32% yield (0.534 g).

MS (APCI) 451 (M+NH$_4$+, 98.9%).

NMR $\delta_H$ (d$_6$-DMSO) 7.88 (2H, s), 7.38-7.34 (4H, m), 3.88 (4H, s), 3.20 (6H, s), 2.64 (6H, s).

f) 7-[[(1R)-2-hydroxy-1-methylethyl]amino]-5-[[[3-methyl-4-(methylsulfonyl)phenyl]methyl]thio]thiazolo[4,5-d]pyrimidin-2(3H)-one The title compound was prepared by the method described in example 16 step b) using the product from example 15 step e) (0.20 g, 0.53 mmol) and the product from example 28 step e) (0.34 g, 0.79 mmol) to yield 11% product as a white lyophylate 0.025 g).

MS (APCI) 441 (M+H+, 100%).

NMR $\delta_H$ (d$_6$-DMSO) 12.40 (1H, s), 7.81 (1H, d), 7.52 (2H, m), 7.33 (1H, d), 4.74 (1H, t), 4.35 (2H, s), 4.19 (1H, m), 3.41 (1H, m), 3.34-3.28 (1H, m), 3.18 (3H, s), 2.61 (3H, s), 1.08 (3H, d).

EXAMPLE 29

5-[[[3-chloro-4-trifluoromethoxy)phenyl]methyl]thio]-7-[[(1R)-2-hydroxy-1-methylethyl]amino]thiazolo[4,5-d]pyrimidin-2(3H)-one a) 3-chloro-4-(trifluoromethoxy)benzenemethanethiol

To a solution of 3-chloro-4-(trifluoromethoxy)benzylbromide (5 g) in ethanol (100 ml) was added thiourea (5 g) and the mixture heated under reflux for 2 hours. The mixture was evaporated to dryness and the residue taken up into water (100 ml). To this solution was added sodium hydroxide pellets (3 g) and the mixture heated under reflux for 1 hour. The mixture was allowed to cool to room temperature and acidified with concentrated hydrochloric acid, the mixture was extracted with ether, dried and evaporated to give the subtitle compound as a colourless waxy solid (3.5 g).

NMR $\delta_H$ (CDCl$_3$) 7.35-7.09 (3H, m), 3.58 (2H, s).

b) 5-[[[3-chloro-4-(trifluoro methoxy)phenyl]methyl]thio]-7-[[(1R)-2-hydroxy-1-methylethyl]amino]thiazolo[4,5-d]pyrimidin-2(3H)-one The title compound was prepared by the method described in example 16 step b) using the product from example 15 step e) (0.40 g, 1.05 mmol) and the product from example 29 step a) (0.71 g, 1.5 mmol) to yield 10% product as a white lyophylate (0.046 g).

MS (APCI) 467 (M+H+, 100%).

NMR $\delta_H$ (d$_6$-DMSO) 12.42 (1H, s), 7.75 (1H, m), 7.52 (2H, m), 7.43 (1H, d), 4.72 (1H, t), 4.34 (2H, d), 4.18 (1H, quintet), 3.46-3.27 (2H, m), 1.07 (3H, d).

EXAMPLE 30

5-[[[2-fluoro-3-(trifluoromethyl)phenyl]methyl]thio]-7-[[(1R)-2-hydroxy-1-methylethyl]amino]thiazolo[4,5-d]pyrimidin-2(3H)-one a) 2-fluoro-3-(trifluoromethyl)benzenemethanethiol

The subtitle compound was prepared from 2-fluoro-(3-trifluoromethyl)benzylbromide (10 g) using the method of example 29 step a)

NMR $\delta_H$ (CDCl$_3$) 7.68-7.18 (3H, m), 3.74 (2H, s), 1.98 (1H, s).

b) 5-[[[2-fluoro-3-(trifluoromethyl)phenyl]methyl]thio]-7-[[(1R)-2-hydroxy-1-methylethyl]amino]thiazolo[4,5-d]pyrimidin-2(3H)-one The title compound was prepared by the method described in example 16 step b) using the product of example 15 step e) (0.47 g, 1.23 mmol) and the product of example 30 step a) (0.775 g, 3.7 mmol) to yield 5% product as a white lyophylate (0.025 g).

MS (APCI) 435 (M+H+, 100%).

NMR $\delta_H$ (d$_6$-DMSO) 12.42 (1H, s), 7.92 (1H, t), 7.68 (1H, t), 7.35 (2H, m), 4.71 (1H, bs), 4.42 (2H, m), 4.16 (1H, quintet), 3.40-3.30 (2H, m), 1.07 (3H, d).

EXAMPLE 31

5-[[(2,3-difluorophenyl)methyl]thio]-7-[2-[(dimethylamino)ethyl]amino]thiazolo[4,5-d]pyrimidin-2(3H)-one monohydrochloride

(a) 2-Bromo-7-chloro-5-[[(2,3-difluorophenyl)methyl]thio]thiazolo[4,5-d]pyrimidine The product of example 4 step (b) (8.0 g) was suspended in bromoform (200 ml) followed by addition of tert-butyl nitrite (8 ml) and the whole heated at 60° C. for 30 minutes. The solvents were removed by reduced pressure and the residue purified by column chromatography (silica—1:1 dichloromethane/isohexane) to give a yellow solid (5.6 g).

MS (APCI) 409/411 (M+H, 100%).

(b) 7-chloro-5-[(2,3-difluorophenylmethyl)thio]-2-methoxythiazolo[4,5-d]pyrimidine The product of example 31 step a) (5.6 g) was suspended in methanol (150 ml) and potassium hydroxide powder (0.77 g) added. The whole was stirred at room temperature for 2 hours. The mixture was adjusted to pH 7 with a few drops of concentrated hydrochloric acid before it was evaporated to dryness. Purified by column chromatography (silica—3:2 to 1:1 isohexane/dichloromethane) to give white solid (2.0 g).

MS (APCI) 360/362 (M+H, 100%).

(c) 7-Chloro-5-[[(2,3-difluorophenyl)methyl]thio]thiazolo[4,5-d]pyrimidin-2(3H)-one The product from example 31 step (b) (2.0 g) was dissolved in dioxan (150 ml) followed by addition of concentrated hydrochloric acid (1 ml) and water (1 ml) and the whole heated at 40° C. for 67 hours. The mixture was evaporated to dryness and purified by column chromatography (silica-dichloromethane) to give a white solid (1.4 g).

MS (APCI) 346/348 (M+H, 100%).

(d) 5-[[(2,3-difluorophenyl)methyl]thio]-7-[2-[(dimethylamino)ethyl]amino]thiazolo[4,5-d]pyrimidin-2(3H)-one monohydrochloride The product from example 31 step (c) (1.4 g) was dissolved in dry tetrahydrofuran (5 ml) and to the solution was added N,N-methylethylenediamine (0.25 g) in a finger bomb which was heated at 80° C. for 24 hours. The solvents were removed by reduced pressure and the residue partitioned between ethyl acetate and brine. The combined organic extracts were dried (sodium sulfate) and evaporated by reduced pressure for the ensuing residue to be purified by column chromatography (silica—5:1 ethyl acetate/methanol) to give the free base as a sticky solid (0.095 g). This was converted to the monohydrochloride by suspending the solid in methanol (10 ml) followed by addition of concentrated hydrochloric acid (3 drops) to ensure dissolution then water (100 ml) for the compound to be freeze dried to give a brown powder (0.080 g).

m.p. 263° C. (dec.)

MS (APCI) 398 (M+H, 100%).

NMR $\delta_H$ ($d_6$-DMSO) 12.57 (1H, s), 10.22 (1H, s), 1.94 (1H, t), 7.40 (1H, m), 7.34 (1H, m), 7.16 (1H, m), 4.43 (2H, s), 3.78 (2H, s), 3.21 (2H, m), 2.78 (6H, d)

EXAMPLE 32

5-[[(2-fluorophenyl methyl]thio]-7-[[(1R)-2-hydroxy-1-methylethyl]amino]thiazolo[4,5-d]pyrimidin-2(3H)-one

(a) 2-[[2-amino-5-[(phenylmethyl)thio]thiazolo[4,5-d]pyrimidin-7-yl]amino]-(2R)-1-propanol The product of example 1 step c) (25.0 g), D-Alaninol (12.3 g) and diisopropylethylamine (26.0 g) were diluted in N-methylpyrrolidinone (250 ml) and stirred at 100° C. for 24 h before cooling and pouring the reaction mixture into $H_2O$ (2.5 l). The precipitate was filtered and dried in vacuo before being preabsorped onto silica gel. Chromatography using EtOAc. 4% MeOH/EtOAc as eluents afforded the desired product as a yellow solid (9.0 g. 32%).

MS (APCI) 347 (M+H, 100%).

(b) 2-[(2-amino-5-mercaptothiazolo[4,5-d]pyrimidin-7-yl)amino]-(2R)-1-propanol Sodium metal was added portionwise to a solution of the product of example 32 step a) (5.0 g) in ammonia (150 ml) until a blue colouration persisted. Ammonium chloride was then added and the solvent allowed to evaporate. The residue was dissolved in $H_2O$ (200 ml) and filtered before neutralising with 2M HCl solution. The grey precipitate was filtered, washed with $H_2O$ (200 ml) and dried in vacuo for 48 h to yield the subtitle compound as a brown solid (3.0 g).

MS (APCI) 258 (M+H, 100%).

(c) 2-[[2-amino-5-[[(2-fluorophenyl)methyl]thio]thiazolo[4,5-d]pyrimidin-7-yl]amino]-(2R)-1-propanol 2-fluorobenzylbromide (0.369 g) was added portionwise to a solution of the product of example 32 step b) (0.5 g) and diisopropylethylamine (0.26 g) in DMSO/N-methylpyrrolidinone (4 ml/0.5 ml) at 50° C. and stirring maintained for 1 h. The mixture was partitioned between $H_2O$ (200 ml) and EtOAc (120 ml). The organics were recovered and washed further with $H_2O$ (200 ml), dried over $MgSO_4$ and concentrated onto silica gel. The subtitle compound was purified by flash chromatography using DCM then EtOAc as eluents to yield a white solid (245 mg, 35%).

MS (APCI) 366 (M+H, 100%)

(d) 2-[[2-bromo-5-[[(2-fluorophenyl)methyl]thio]thiazolo[4,5-d]pyrimidin-7-yl]amino]-(2R)-1-propanol Isoamyl nitrite (0.3 ml) was added to a suspension of the product of example 32 step c) (0.23 g) in bromoform (15 ml) and acetonitrile (15 ml) at 50° C. Stirring was maintained for 10 min before concentrating to approximately, 3 ml. The residue was purified by column chromatography using 20% EtOAc/DCM as eluent to yield the subtitle compound as a yellow solid (102 mg, 38%).

MS (APCI) 429 (M+H, 100%).

(e) 2-[[5-[[(2-fluorophenyl)methyl]thio]-2-methoxythiazolo[4,5-d]pyrimidin-7-yl]amino]-(2R)-1-propanol Potassium hydroxide (27 mg) was added to a solution of the product of example 32 step d) (0.1 g) in MeOH (10 ml). The mixture was stirred for 24 h before neutralising to pH 7 with 2M HCl solution. The volatiles were removed in vacuo and the product used directly in the following step.
MS (APCI) 381 (M+H, 100%).

(f) 5-[[(2-fluorophenyl)methyl]thio]-7-[[(1R)-2-hydroxy-1-methylethyl]amino]thiazolo[4,5-d]pyrimidin-2(3H)-one The product of example 32 step e) was dissolved in 1,4-dioxane (50 ml), $H_2O$ (1 ml) and concentrated HCl solution (0.5 ml) and stirred for 20 h at 40° C. The volatiles were removed under reduced-pressure and the crude product purified by preparative HPLC to afford the subtitle compound as a white solid (21 mg).
MS (APCI) 367 (M+H, 100%)
NMR δH ($d_6$-DMSO) 12.40 (1H, s), 8.14-7.11 (5H, m), 4.72 (1H, t), 4.35 (2H, m), 4.22 (1H, m), 3.47-3.29 (2H, m), 1.10 (3H, d)

EXAMPLE 33

7-[[(1R)-2-hydroxy-1-methylethyl]amino]-5-[[(2-methoxyphenyl)methyl]thio]thiazolo[4,5-d]pyrimidin-2(3H)-one (a) 2-[[2-amino-5-[[(2-methoxyphenyl)methyl]thio]thiazolo[4,5-d]pyrimidin-7-yl]amino]-(2R)-1-propanol Prepared by the method of example 32 step c), using the product of example 32 step b).
MS (APCI) 378 (M+H$^+$, 10%).

(b) 2-[[2-bromo-5-[[(2-methoxyphenyl)methyl]thio]thiazolo[4,5-d]pyrimidin-7-yl]amino]-(2R)-1-propanol Prepared by the method of example 32 step d), using the product of example 33 step a).
MS (APCI) 441 (M+H$^+$, 100%).

(c) 2-[[2-methoxy-5-[[(2-methoxyphenyl)methyl]thio]thiazolo[4,5-d]pyrimidin-7-yl]amino]-(2R)-1-propanol Prepared by the method of example 32 step e), using the product of example 33 step b).
MS (APCI) 393 (M+H$^+$, 100%).

(d) 7-[[(1R)-2-hydroxy-1-methylethyl]amino]-5-[[(2-methoxyphenyl)methyl]thio]thiazolo[4,5-d]pyrimidin-2(3H)-one Prepared by the method of example 32 step f), using the product of example 33 step c).
MS (APCI) 379 (M+H$^+$, 100%).
NMR δH ($d_6$-DMSO) 7.40 (1H, dd), 7.22 (1H, dt), 6.97 (1H, d), 6.84 (1H, dt), 6.00 (1H, d), 4.25 (2H, m), 4.15 (1H, m), 3.83 (3H, s), 3.48-3.31 (2H, m), 1.10 (3H, d).

EXAMPLE 34

7-[[(1R)-2-hydroxy-1-methylethyl]amino]-5-[(2-phenoxyethyl)thio]thiazolo[4,5-d]pyrimidin-2(3H)-one (a) 2-[[2-amino-5-[(2-phenoxyethyl)thio]thiazolo[4,5-d]pyrimidin-7-yl]amino]-(2R)-1-propanol Prepared by the method of example 32 step c), using the product of example 32 step b).
MS (APCI) 378 (M+H$^+$, 100%).

(b) 2-[[2-bromo-5-[(2-phenoxyethyl)thio]thiazolo[4,5-d]pyrimidin-7-yl]amino]-(2R)-1-propanol Prepared by the method of example 32 step d), using the product of example 34 step a).
MS (APCI) 441 (M+H$^+$, 100%).

(c) 2-[[2-methoxy-5-[(2-phenoxyethyl)thio]thiazolo[4,5-d]pyrimidin-7-yl]amino]-(2R)-1-propanol Prepared by the method of example 32 step e), using the product of example 34 step b).
MS (APCI) 393 (M+H$^+$, 100%).

(d) 7-[[(1R)-2-hydroxy-1-methylethyl]amino]-5-[(2-phenoxyethyl)thio]thiazolo[4,5-d]pyrimidin-2(3H)-one Prepared by the method of example 32 step f), using the product of example 34 step c).
MS (APCI) 379 (M+H$^+$, 100%).
NMR-δH ($d_6$-DMSO) 12.37 (1H, s), 7.30-7.26 (3H, m), 6.96-6.91 (3H, m), 4.71 (1H, t), 4.23-4.14 (3H, m), 3.46-3.28 (4H, m), 1.08 (3H, d).

EXAMPLE 35

7-[[(1R)-2-hydroxy-1-methylethyl]amino]-5-[[(3-methylphenyl)methyl]thio]thiazolo[4,5-d]pyrimidin-2(3H)-one (a) 2-[[2-amino-5-[[(3-methylphenyl)methyl]thio]thiazolo[4,5-d]pyrimidin-7-yl]amino]-(2R)-1-propanol Prepared by the method of example 32 step c), using the product of example 32 step b).
MS (APCI) 362 (M+H$^+$, 100%).

(b) 2-[[2-bromo-5-[[(3-methylphenyl)methyl]thio]thiazolo[4,5-d]pyrimidin-7-yl]amino]-(2R)-1-propanol Prepared by the method of example 32 step d), using the product of example 35 step a).
MS (APCI) 425 (M+H$^+$, 100%).

(c) 2-[[2-methoxy-5-[[(3-methylphenyl)methyl]thio]thiazolo[4,5-d]pyrimidin-7-yl]amino]-(2R)-1-propanol Prepared by the method of example 32 step e), using the product of example 35 step b).
MS (APCI) 377 (M+H$^+$, 100%).

(d) 7-[[(1R)-2-hydroxy-1-methylethyl]amino]-5-[[(3-methylphenyl)methyl]thio]thiazolo[4,5-d]pyrimidin-2(3H)-one Prepared by the method of example 32 step f), using the product of example 35 step c).
MS (APCI) 363 (M+H$^+$, 100%).
NMR δH (d$_6$-DMSO) 12.37 (1H, s), 7.23-7.16 (4H, m), 7.04 (1H, d), 4.73 (1H, t), 4.28 (2H, m), 4.24 (1H, m), 3.48-3.30 (2H, m), 2.28 (3H, s), 1.11 (3H, d).

EXAMPLE 36

5-[[(2-fluoro-3-methylphenyl)methyl]thio]-7-[[(1R)-2-hydroxy-1-methylethyl]amino]thiazolo[4,5-d]pyrimidin-2(3)-one (a) 2-[[2-amino-5-[[(2-fluoro-3-methylphenyl)methyl]thio]thiazolo[4,5-d]pyrimidin-7-yl]amino]-(2R)-1-propanol Prepared by the method of example 32 step c), using the product of example 32 step b).
MS (APCI) 380 (M+H$^+$, 100%).

(b) 2-[[2-bromo-5-[[(2-fluoro-3-methylphenyl)methyl]thio]thiazolo[4,5-d]pyrimidin-7-yl]amino]-(2R)-1-propanol Prepared by the method of example 32 step d), using the product of example 36 step a).
MS (APCI) 443 (M+H$^+$, 100%).

(c) 2-[[5-[[(2-fluoro-3-methylphenyl)methy]thio]-2-methoxythiazolo[4,5-d]pyrimidin-7-yl]amino]-(2R)-1-propanol Prepared by the method of example 32 step e), using the product of example 36 step b).
MS (APCI) 395 (M+H$^+$, 100%).

(d) 5-[[(2-fluoro-3-methylphenyl)methyl]thio]-7-[[(1R)-2-hydroxy-1-methylethyl]amino]thiazolo[4,5-d]pyrimidin-2(3)-one Prepared by the method of example 12 step f), using the product of example 36 step c).
MS (APCI) 381 (M+H$^+$, 100%).
NMR δH (d$_6$-DMSO) 12.39 (1H, s), 7.37-7.00 (4H, m), 4.72 (1H, t), 4.33 (2H, m), 4.22 is (1H, m), 3.47-3.30 (2H, m), 2.23 (3H, s), 1.11 (3H, d)

EXAMPLE 37

5-[[(3-chlorophenyl)methyl]thio]-7-[[(1R)-2-hydroxy-1-methylethyl]amino]thiazolo[4,5d]pyrimidin-2(3H)-one (a) 2-[[2-amino-5-[[(3-chlorophenyl)methyl]thio]thiazolo[4,5-d]pyrimidin-7-yl]amino]-(2R)-1-propanol Prepared by the method of example 32 step c), using the product of example 32 step b).
MS (APCI) 382 (M+H$^+$, 100%).

(b) 2-[[2-bromo-5-[[(3-chlorophenyl)methyl]thio]thiazolo[4,5-d]pyrimidin-7-yl]amino]-(2R)-1-propanol Prepared by the method of example 32 step d), using the product of example 37 step a).
MS (APCI) 445 (M+H$^+$, 100%).

(c) 2-[[5-[[(3-chlorophenyl)methyl]thio]-2-methoxythiazolo[4,5-d]pyrimidin-7-yl]amino]-(2R)-1-propanol Prepared by the method of example 32 step e), using the product of example 37 step b).
MS (APCI) 397 (M+H$^+$, 100%).

(d) 5-[[(3-chlorophenyl)methyl]thio]-7-[[(1R)-2-hydroxy-1-methylethyl]amino]thiazolo[4,5-d]pyrimidin-2(3H)-one Prepared by the method of example 32 step f), using the product of example 37 step c).
MS (APCI) 383 (M+H$^+$, 100%).
NMR δH (d$_6$-DMSO) 12.40 (1H, s), 7.49 (1H, d), 7.43-7.30 (4H, m), 4.72 (1H, t), 4.32 (2H, m), 4.21 (1H, m), 3.48-3.26 (2H, m), 1.09 (3H, d).

EXAMPLE 38

5-[[(3-bromophenyl)methyl]thio]-7-[[(1R)-2-hydroxy-1-methylethyl]amino]thiazolo[4,5-d]pyrimidin-2(3H)-one (a) 2-[[2-amino-5-[[(3-bromophenyl)methyl]thio]thiazolo[4,5-d]pyrimidin-7-yl]amino]-(2R)-1-propanol Prepared by the method of example 32 step c), using the product of example 32 step b).
MS (APCI) 426 (M+H$^+$, 100%).

(b) 2-[[2-bromo-5-[[(3-bromophenyl)methyl]thio]thiazolo[4,5-d]pyrimidin-7-yl]amino]-(2R)-1-propanol Prepared by the method of example 32 step d), using the product of example 38 step a).
MS (APCI) 491 (M+H$^+$, 100%), (c) 2-[[5-[[(3-bromophenyl)methyl]thio]-2-methoxythiazolo[4,5-d]pyrimidin-7-yl]amino]-(2R)-1-propanol Prepared by the method of example 32 step e), using the product of example 38 step b).
MS (APCI) 443 (M+H$^+$, 100%).

(d) 5-[[(3-bromophenyl)methyl]thio]-7-[[(1R)-2-hydroxy-1-methylethyl]amino]thiazolo[4,5-d]pyrimidin-2(3H)-one Prepared by the method of example 32 step f), using the product of example 38 step c).
MS (APCI) 427 (M+H$^+$, 100%).
NMR δH (d$_6$-DMSO) 12.40 (1H, s), 7.63 (1H, t), 7.16-7.24 (4H, m), 4.72 (1H, t), 4.31 (2H, m), 4.21 (1H, m), 3.48-3.26 (2H, m), 1.10 (3H, d)

EXAMPLE 39

5-[[[4-(difluoromethoxy)phenyl]methyl]thio]-7-[[(1R)-2-hydroxy-1-methylethyl]amino]thiazolo[4,5-d]pyrimidin-2(3H)-one (a) 2-[[2-amino-5-[[[4-(difluoromethoxy)phenyl]methyl]thio]thiazolo[4,5-d]pyrimidin-7-yl]amino]-(2R)-1-propanol Prepared by the method of example 32 step c), using the product of example 32 step b).
MS (APCI) 414 (M+H$^+$, 100%).

(b) 2-[[2-bromo-5-[[[4-(difluoromethoxy)phenyl]methyl]thio]thiazolo[4,5-d]pyrimidin-7-yl]amino]-(2R)-1-propanol Prepared by the method of example 32 step d), using the product of example 39 step a).
MS (APCI) 477 (M+H$^+$, 100%).

(c) 2-[[5-[[[4-(difluoromethoxy)phenyl]methyl]thio]-2-methoxythiazolo[4,5-d]pyrimidin-7-yl]amino]-(2R)-1-propanol Prepared by the method of example 32 step e), using the product of example 39 step b).
MS (APCI) 429 (M+H$^+$, 100%).

(d) 5-[[[4-(difluoromethoxy)phenyl]methyl]thio]-7-[[(1R)-2-hydroxy-1-methylethyl]amino]thiazolo[4,5-d]pyrimidin-2(3H)-one Prepared by the method of example 32 step f), using the product of example 39 step c).
MS (APCI) 415 (M+H$^+$, 100%).
NMR δH (d$_6$-DMSO) 12.38 (1H, s), 7.48 (2H, dt), 7.26 (1H, d), 7.19 (1H, t), 7.11 (2H, dd), 4.73 (1H, t), 4.31 (2H, m), 4.21 (1H, m), 3.47-3.30 (2H, m), 1.10 (3H, d)

EXAMPLE 40

(+/−)-5-[[(2,3-difluorophenyl)methyl]thio]-7-[[2-hydroxy-1-(methoxymethyl)ethyl]amino]thiazolo[4,5-d]pyrimidin-2(3H)-one (a) (+/−)-2-amino-3-methoxy-1-propanol hydrochloride To a suspension of DL-3-methoxy-alanine (1.0 g) in dry THF (100 ml) was added borane methylsulfide complex (10 ml) and the mixture heated under reflux for 16 hours. The mixture was then quenched with methanol while at reflux, evaporated to dryness and the residue taken up into methanolic hydrogen chloride (100 ml) and heated under reflux for a further 2 hours, evaporated to dryness to give the subtitle compound as a colourless gum (1.0 g).
NMR δ$_H$ (D$_2$O) 3.40 (3H, s), 3.53-3.74 (4H, m), 3.81 (1H, m)

(b) (+/−)-2-[[2-amino-5-[[(2,3-difluorophenyl)methyl]thio]thiazolo[4,5-d]pyrimidin-7-yl]amino]-3-methoxy-1-propanol Prepared by the method of example 12 step a) using the product of example 4 step b) and the product of example 40 step a).
MS (APCI) 414 (M+H$^+$, 100%).

(c) (+/−)-2-[[2-chloro-5-[[(2,3-difluorophenyl)methyl]thio]thiazolo[4,5-d]pyrimidin-7-yl]amino]-3-methoxy-1-propanol To a solution of the product from example 40 step b) (1.0 g) in a mixture of concentrated hydrochloric acid (40 ml) and water (32 ml) cooled in ice water was added a solution of sodium nitrite (0.4 g) in water (5 mL), stirred at this temp for 2 hours. The mixture was then extracted into ethyl acetate, dried and evaporated to give the subtitle compound, (0.6 g).
MS (APCI) 434 (M+H$^+$, 100%).

(d) (+/−)-2-[[5-[[(2,3-difluorophenyl)methyl]thio]-2-methoxythiazolo[4,5-d]pyrimidin-7-yl]amino]-3-methoxy-1-propanol, Prepared by the method of example 1 step f), using the product of example 40 step c).
MS (APCI) 429 (M+H$^+$, 100%).

(e) (+/−)-5-[[(2,3-difluorophenyl)methyl]thio]-7-[[2-hydroxy-1-(methoxymethyl)ethyl]amino]thiazolo[4,5-d]pyrimidin-2(3H)-one Prepared by the method of example 1 step g), using the product of example 40 step d).
MS (APCI) 415 (M+H$^+$, 100%).

EXAMPLE 41

7-[[2-hydroxy-1-(hydroxymethyl)ethyl]amino]-5-[(phenylmethyl)thio]thiazolo[4,5-d]pyrimidin-2(3H)-one (a) 2-[[2-amino-5-[(phenylmethyl)thio]thiazolo[4,5-d]pyrimidin-7-yl]amino]-1,3-propanediol Prepared by the method of example 12 step a) using the product of example 1 step c) and 2-amino-1,3-propanediol.
MS (APCI) 364 (M+H$^+$, 100%).
NMR δH (d$_6$-DMSO) 7.42-7.38 (1H, m), 7.28 (1H, t), 7.22 (1H, t), 5.30 (1H, d), 4.63 (1H, bs), 4.28 (2H, s), 4.03 (1H, m), 3.54-3.40 (4H, m).

(b) 2-[[2-chloro-5-[(phenylmethyl)thio]thiazolo[4,5-d]pyrimidin-7-yl]amino]-1,3-propanediol, Prepared by the method of example 40 step c) and the product of example 41 step a)
MS (APCI) 384 (M+H$^+$, 100%).

(c) 2-[[2-methoxy-5-[(phenylmethyl)thio]thiazolo[4,5-d]pyrimidin-7-yl]amino]-1,3-propanediol, Prepared by the method of example 1 step f) and the product of example 41 step b)
MS (APCI) 379 (M+H$^+$, 100%).

(d) 7-[[2-hydroxy-1-(hydroxymethyl)ethyl]amino]-5-[(phenylmethyl)thio]thiazolo[4,5-d]pyrimidin-2(3H)-one Prepared by the method of example 1 step g) and the product of example 41 step c)
MS (APCI) 365 (M+H$^+$, 100%).

EXAMPLE 42

5-[[(2-bromophenyl)methyl]thio]-7-[[(1R)-2-hydroxy-1-methylethyl]amino]thiazolo[4,5d]pyrimidin-2(3H)-one (a) 2-[[2-amino-5-[[(2-bromophenyl)methyl]thio]thiazolo[4,5-d]pyrimidin-7-yl]amino]-(2R)-1-propanol Prepared by the method of example 32 step c), using the product of example 32 step b).
MS (APCI) 428 (M+H$^+$, 100%).

(b) 2-[[2-bromo-5-[[(2-bromophenyl)methyl]thio]thiazolo[4,5-d]pyrimidin-7-yl]amino]-(2R)-1-propanol Prepared by the method of example 1 step e), using the product of example 42 step a).
MS (APCI) 491 (M+H$^+$, 100%).

(c) 2-[[5-[[(2-bromophenyl)methyl]thio]-2-methoxythiazolo[4,5-d]pyrimidin-7-yl]amino]-(2R)-1-propanol Prepared by the method of example 1 step f), using the product of example 42 step b).
MS (APCI) 443 (M+H$^+$, 100%).

(d) 5-[[(2-bromophenyl)methyl]thio]-7-[[(1R)-2-hydroxy-1-methylethyl]amino]thiazolo[4,5-d]pyrimidin-2(3H)-one Prepared by the method of example 1 step g), using the product of example 42 step c).
MS (APCI) 427 (M+H$^+$, 100%).
NMR δH (d$_6$-DMSO) 12.41 (1H, s), 7.65-7.14 (5H, m), 4.72 (1H, t), 4.42 (2H, s), 4.21 (1H, m), 3.47-3.30 (2H, m), 1.10 (3H, d)

EXAMPLE 43

5-[[(2,3-Difluorophenyl)methyl]thio]-7-[[(1R)-2-hydroxy-1-methylethyl]amino]thiazolo[4,5-d]pyrimidin-2(3H)-one sodium salt The product from example 5 step d) was suspended in water and to this suspension was added 1 equivalent of 0.1 N sodium hydroxide solution, followed by the addition of a small aliquot of tetrahydrofuran to aid dissolution. The resultant solution was then lyophilised to give the title compound as a colourless solid.
MP 218-220° C.
MS (APCI) 385 (M+H$^+$, 100%).
NMR δH (d$_6$-DMSO) 7.39-7.09 (3H, m), 5.60 (1H, d), 4.65 (1H, m), 4.34 (2H, q), 4.09 (1H, m), 3.44-3.27 (2H, m), 1.06 (3H, d).

EXAMPLE 44

5-[[3-Chloro-2-fluorophenyl)methyl]thio]-7-[[(1R)-2-hydroxy-1-methylethyl]amino]thiazolo[4,5-d]pyrimidin-2(3H)-one sodium salt Prepared as in example 43 using the product of example 17 step b)
MS (APCI) 401 (M+H$^+$, 100%).

EXAMPLE 45

(+/−)-5-[[(2,3-difluorophenyl)methyl]thio]-7-[[2-hydroxy-1-(methoxymethyl)ethyl]amino]thiazolo[4,5-d]pyrimidin-2(3H)-one sodium salt Prepared by the method of example 43 using the product of example 40 step e).
MP >250° C.
MS (APCI) 415 (M+H$^+$, 100%).
NMR δH (d$_6$-DMSO) 7.39-7.04 (3H, m), 5.51 (1H, d), 4.68 (1H, t), 4.34 (2H, q), 4.22 (1H, m), 3.51-3.35 (4H, m), 3.32 (3H, s).

EXAMPLE 46

7-[[2-hydroxy-1-hydroxymethyl)ethyl]amino]-5-[(phenylmethyl)thio]thiazolo[4,5-d]pyrimidin-2(3H)-one sodium salt Prepared by the method of example 43 using the product from example 41 step d)
MP 231-2° C.
MS (APCI) 365 (M+H$^+$, 100%).
NMR 8H (d$_6$-DMSO) 7.41-7.18 (5H, m), 5.30 (1H, d), 4.63 (2H, s), 4.28 (2H, s), 4.06 (1H, m), 3.50 (4H, m).

EXAMPLE 47

7-[[(1R)-2-Hydroxy-1-methylethyl]amino]-5-[(phenylmethyl)thio]thiazolo[4,5-d]pyrimidin-2(3H)-one sodium salt Prepared by the method of example 43 using the product of example 3 step d).
MP (shrinks 110) melts 221-225° C.
MS (APCI) 349 (M+H$^+$, 100%).
NMR δH (d$_6$-DMSO) 7.41-7.18 (5H, m), 5.58 (1H, d), 4.65 (1H, t), 4.28 (2H, q), 4.11 (1H, m), 3.49-3.31 (2H, m), 1.08 (3H, d).

EXAMPLE 48

5-[(5-chloro-1,2,3-thiadiazol-4-yl)thio]-7-[[(1R)-2-hydroxy-1-methylethyl]amino]-thiazolo[4,5-d]pyrimidin-2(3H)-one (a) (2R)-2-[[2-amino-5-[(5-chloro-1,2,3-thiadiazol-4-yl)thio]thiazolo[4,5-d]pyrimidin-7-yl]amino]-1-propanol Prepared by the method of example 32 step c), using the product of example 32 step b) and 5-chloro-4-(chloromethyl)-1,2,3-thiadiazole.
MS (APCI) 390 (M+H$^+$, 100%).

(b) (2R)-2-[[2-chloro-5-[[(5-chloro-1,2,3-thiadiazol-4-yl)methyl]thio]thiazolo[4,5-d]pyrimidin-7-yl]amino]-1-propanol Prepared by the method of example 40 step c) and using the product of example 48 step a)
MS (APCI) 409 (M+H$^+$, 100%).

(c) (2R)-2-[[5-[[(5-chloro-1,2,3-thiadiazol-4-yl)methyl]thio]-2-methoxythiazolo[4,5-d]pyrimidin-7-yl]amino]-1-propanol Prepared by the method of example 1 step f) and using the product of example 48 step b)
MS (APCI) 405 (M+H$^+$, 100%).

(d) 5-[(5 chloro-1,2,3-thiadiazol-4-yl)thio]-7-[[(1R)-2-hydroxy-1-methylethyl]amino]-thiazolo[4,5-d]pyrimidin-2(3H)-one Prepared by the method of example 1 step g) and using the product of example 48 step c)
MS (APCI) 391(M+H$^+$, 100%).
NMR δH (d$_6$-DMSO) 12.39 (1H, s), 7.39 (1H, d), 4.76 (2H, AB), 4.70 (1H, t), 4.24 (1H, m), 3.48-3.30 (2H, m), 1.11 (3H, d)

Pharmacological Data
Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283-16291). hrCXCR2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 μg/ml soybean trypsin inhibitor, 3 mM benzamidine, 0.5 μg/ml leupeptin and 100 μg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH$_2$PO$_4$), 0.1% (w/v) gelatin and 10% (v/v) glycerol.

All assays were performed in a 96-well MultiScreen 0.45 μm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1% (w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter.

The compounds of formula (I) according to the Examples were found to have IC$_{50}$ values of less than (<) 10 μM.

Intracellular Calcium Mobilisation Assay

Human neutrophils were prepared from EDTA-treated peripheral blood, as previously described (Baly et al. (1997) Methods in Enzymology 287 pp 70-72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp 513-519). Cells were loaded for 1 hour at 37° C. in loading buffer (storage buffer with 0.1% (w/v) gelatin) containing 5 μM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.)

The compounds of formula (I) according to the Examples were tested and found to be antagonists of the CXCR2 receptor in human neutrophils.

What is claimed is:

1. The compound 5-[[2,3-Difluorophenyl)methyl]thio]-7-[[(1R)-2-hydroxy-1-methylethyl]amino]thiazolo[4,5-d]pyrimidin-2(3H)-one, or a pharmaceutically acceptable salt thereof.

2. The sodium salt of 5-[[(2,3-Difluorophenyl)methyl]thio]-7-[[(1R)-2-hydroxy-1-methylethyl]amino]thiazolo[4,5-d]pyrimidin-2(3H)-one.

3. A pharmaceutical composition comprising the compound 5-[[2,3-Difluorophenyl)methyl]thio]-7-[[(1R)-2-hydroxy-1-methylethyl]amino]thiazolo[4,5-d]pyrimidin-2 (3H)-one, or a pharmaceutically acceptable salt thereof, and a pharmaceutically acceptable adjuvant, diluent, or carrier.

4. A pharmaceutical composition comprising the sodium salt of 5-[[2,3-Difluorophenyl)methyl]thio]-7-[[(1R)-2-hydroxy-1-methylethyl]amino]thiazolo[4,5-d]pyrimidin-2 (3H)-one, or a pharmaceutically acceptable salt thereof, and a pharmaceutically acceptable adjuvant, diluent, or carrier.

* * * * *

UNITED STATES PATENT AND TRADEMARK OFFICE
CERTIFICATE OF CORRECTION

PATENT NO. : 8,143,261 B2  
APPLICATION NO. : 12/432224  
DATED : March 27, 2012  
INVENTOR(S) : Paul Andrew Willis Page 1 of 1

It is certified that error appears in the above-identified patent and that said Letters Patent is hereby corrected as shown below:

On the Title page, Item [75], Line 2, please delete "Roger Bonnert" and insert --Roger Victor Bonnert--;

On the Title page (Abstract), Line 3, please delete "thereof," and insert --thereof;--, therefor.

Signed and Sealed this  
Twelfth Day of June, 2012

David J. Kappos  
*Director of the United States Patent and Trademark Office*